United States Patent
Kauvar et al.

(10) Patent No.: US 7,413,868 B2
(45) Date of Patent: Aug. 19, 2008

(54) USE OF PARTICULATE LABELS IN BIOANALYTE DETECTION METHODS

(75) Inventors: Lawrence M. Kauvar, San Francisco, CA (US); Remy Cromer, Saratoga, CA (US); William D. Harriman, Alameda, CA (US); Ellen J. Collarini, Oakland, CA (US)

(73) Assignee: Trellis Bioscience, Inc., South San Francisco, CA (US)

( * ) Notice: Subject to any disclaimer, the term of this patent is extended or adjusted under 35 U.S.C. 154(b) by 412 days.

(21) Appl. No.: 10/981,130

(22) Filed: Nov. 3, 2004

(65) Prior Publication Data

US 2005/0106641 A1 May 19, 2005

Related U.S. Application Data

(60) Provisional application No. 60/517,651, filed on Nov. 5, 2003, provisional application No. 60/517,713, filed on Nov. 5, 2003.

(51) Int. Cl.
*G01N 33/53* (2006.01)
*G01N 33/567* (2006.01)

(52) U.S. Cl. ............... 435/7.2; 435/7.23; 435/7.24; 435/7.92; 435/287.2; 435/287.7; 435/288.3; 435/372.2; 435/372.3; 436/518; 436/522; 436/524; 436/528; 436/46; 436/56; 436/63; 436/172; 436/177

(58) Field of Classification Search ............... 435/7.1, 435/7.21–7.24, 7.92, 7.94, 372.2, 372.3, 435/287.9, 287.2, 968, 973; 436/518, 521, 436/522, 77, 524–530, 533, 546, 10, 17, 436/63, 64, 172, 46, 56
See application file for complete search history.

(56) References Cited

U.S. PATENT DOCUMENTS

| | | | |
|---|---|---|---|
| 5,773,222 A | 6/1998 | Scott | |
| 6,214,560 B1 | 4/2001 | Yguerabide et al. | |
| 6,410,252 B1 * | 6/2002 | Lehmann et al. | 435/7.94 |
| 6,492,125 B2 | 12/2002 | Kauvar et al. | |
| 6,642,062 B2 * | 11/2003 | Kauvar et al. | 436/518 |
| 6,673,554 B1 | 1/2004 | Kauvar | |
| 6,872,574 B2 * | 3/2005 | Cravatt et al. | 436/119 |
| 6,972,198 B2 * | 12/2005 | Craig et al. | 436/164 |
| 2005/0250155 A1 * | 11/2005 | Lesko et al. | 435/6 |

FOREIGN PATENT DOCUMENTS

EP 0 577 092 1/1994

OTHER PUBLICATIONS

Han et al., Quantum-dot-tagged for multiplexed optical coding of biomolecules, Nature Biotechnology 19:631-635 (Jul. 2001).*

(Continued)

*Primary Examiner*—Gailene R Gabel
(74) *Attorney, Agent, or Firm*—Morrison & Foerster LLP

(57) ABSTRACT

New applications for the use of distinguishable particulate labels available in a variety of hues and sized in the submicron range are described. These applications include profiling of cellular components, obtaining secretion patterns, identifying a multiplicity of components in chromatographic or electrophoretic techniques and identification of desired immunoglobulin secreting cells.

18 Claims, 7 Drawing Sheets

A

B

OTHER PUBLICATIONS

Han et al., Nat. Biotechnol. (2001) 19:631-635.
Nicewarner-Pena et al., Science (2001) 294:137-141.
Gazagne et al., Journal of Immunological Methods (2003) 283(1-2):91-98.
Radosevic et al., Journal of Immunological Methods (2003) 272(1-2):219-233.
Supplementary Partial European Search Report for EP 04818350.3, mailed Jun. 22, 2007, 9 pages.
Watkins et al., Analytical Biochemistry (1998) 256(2):169-177.

* cited by examiner

  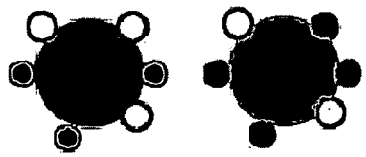
Figure 1A  Figure 1B  Figure 1C
Figure 1
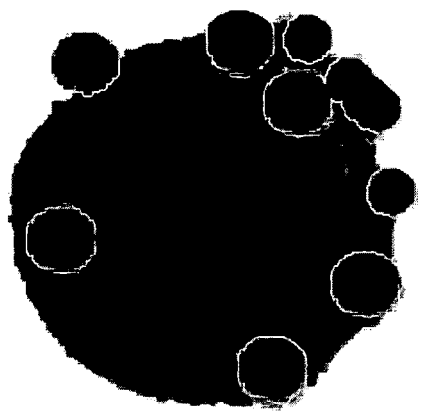
Figure 2

(a) Bifunctional linkage

(b) Hydrophobic attraction

(c) Silanization

(d) Electrostatic attraction

(e) Nanobeads

USE OF PARTICULATE LABELS IN BIOANALYTE DETECTION METHODS

CROSS-REFERENCE TO RELATED APPLICATIONS

This application claims benefit of U.S. provisional applications 60/517,651 filed 5 Nov. 2003 and 60/517,713 filed 5 Nov. 2003. The contents of these documents are incorporated herein by reference.

TECHNICAL FIELD

The invention relates to methods that utilize submicron sized particulate labels containing signal-generating moieties whose characteristic hue can be adjusted over a range of distinguishable types, thus permitting a variety of multiplexed assays. The invention also relates to assays for which multiplexed particles provide a preferred but not exclusive embodiment. The invention also relates to the field of clinical investigations of new drugs and assessment of responses of individual subjects to treatment protocols.

BACKGROUND ART

It is often desirable to test a sample for reactivity against a multiplicity of reagents. For example, in cytokine secretion profiling, the ability of the secreted proteins from a particular tissue to immunoreact with a panel of antibodies raised with respect to the family of antigens is required, with tens to hundreds of family members of potential interest. In this instance, detection of the presence of the antibody-antigen complex normally requires that either a label be attached to the antibody in the complex or that a second antibody be bound to the first antibody where the second antibody has a label attached to it. Then, detection of the label confirms the presence of the antibody-antigen complex in the sample.

Commonly, the second antibody is a biotinylated goat anti-primary IgG that will react with avidin-horse radish peroxidase and, in the presence of a redox sensitive color indicator and substrate (hydrogen peroxide), result in a change in color, on a filter for example, indicating the presence of the antibody-antigen complex. Alternatively, instead of biotinylating the secondary antibody, an $^{125}$I-labeled secondary antibody can be used. If an $^{125}$I-label is used, exposure of the filter to X-ray film will allow for the detection of the antibody-antigen complex.

Often the signal emitted from these labels is not strong enough to be detected due to the low expression level of the protein of interest or limited supply of specimen. In addition, although it is possible to detect the presence of several different antigens in a sample by using an antibody directed towards each antigen, a common readout for all antibodies makes it impossible to clearly distinguish one antigen-antibody complex from another without prior fractionation (e.g., by gel electrophoresis) or parallel assay of specimen aliquots (including capture on discrete locations on a chip or a combinatorially colored particle set). To address the sensitivity issue, it would be advantageous to have a label that emits a signal strong enough to allow detection of antigens in a sample even if the antigen is present at low amounts. It would further be advantageous to determine the presence of multiple antigens in a complex mixture by virtue of a family of such labels with distinguishable signals. For example, serological tissue typing for HLA antigens probes ~6 genetic loci for dozens to hundreds of allelic variants at each locus. Any given individual will at most express 2 alleles for each locus, but hundreds of separate assays are needed to accomplish the typing. With multiplexing, all the assays can be run on one specimen, providing a more efficient system. For an application such as this, it is important that the staining reagents themselves be multiplexed, as contrasted to multiplexed binding surfaces to which a single staining reagent binds.

An even more compelling need for sensitive, highly multiplexed detection is readily apparent in the case of cytokine secretion assays in which the proteins secreted from a single cell are captured on the underlying surface and then analyzed in situ. Such assays have heretofore only been described at the 2-plex level, with the vast majority of work at the 1-plex level to avoid the increased assay complexity inherent in previously available multiplexing approaches. Increasing the multiplexing capacity enables identification of novel T-cell subtypes that would require immense effort to discover by looking only at pairwise combinations of the two dozen or more cytokines. More generally, normal cell to cell variation makes it difficult to identify novel cell types based on multivariate properties when only two or three properties are measured per cell.

It is also desirable to multiplex DNA sequencing. Originally, sequencing by the chain-termination method involves the synthesis of a DNA strand by a DNA polymerase using a single stranded template. Synthesis initiated at the site where an oligonucleotide primer anneals to the template was terminated by the incorporation of a low level of radio-labeled nucleotide analog (ddNTP) into the elongation reagent cocktail. When proper mixtures of dNTP's and one of the four ddNTP's are used, polymerization terminates randomly at each possible site allowing for the sequence of the DNA to be read following size separation by gel or capillary electrophoresis. Four parallel reactions are fractionated in parallel lanes to identify the base at each termination length. More recently, the four reactions have each been terminated using a ddNTP conjugated to a different color of fluorescent dye, and all four reaction product mixtures fractionated together in one lane of a gel or one capillary electrophoresis channel. Thus, what was originally a 1-plex assay became a 4-plex assay. With the additional multiplexing capacity of the present invention, more than one DNA template could be sequenced in a single lane or capillary.

High detection sensitivity is also important for multiplexed DNA sequencing to avoid overloading the gel or capillary which can perturb the migration of the DNA molecules. The signal emitted from conventional radioactive or fluorescent dye-based labels is often not strong enough to be detected without extensive amplification of the DNA; a more sensitive label enables decreasing assay complexity and the associated potential for artifactual results. And, with the extra data channels provided by sensitive multiplexing, an internal sizing ladder can be included in every lane.

One embodiment of suitable multiplexing technology has been previously described in detail in U.S. Pat. Nos. 6,642,062 and 6,492,125. Briefly, in a preferred embodiment latex (polystyrene) particles are impregnated with organic dye fluors in varying ratios to generate a combinatorially coded set of labels. Alternatively, fluorescent labels comprising nanocrystalline semiconductor structures of various types, commonly called quantum dots, may be employed. Such particles can also be coupled to biorecognition molecules, or can be used in other particulates in varied ratios as substitutes for fluorescent dyes. Han, M. Y., et al., *Nat. Biotechnol.* (2001) 19:631-635 describes polystyrene particles embedded with multicolor CdSe quantum dots at various color and intensity combinations. Based on entirely different principles, Nicewarner-Pena, S. R., et al., *Science* (2001) 294:137-141 have reported a metallic nanobarcoding technology for multiplexed bioassays.

The use of submicron particles that are bright enough for single particle detection enables a variety of assay formats not accessible to conventional signal generating labels for which integrated intensity of a population of labels is measured. In addition to latex microspheres and quantum dots, for which fluorescence is the signal, other possible signals include phosphorescence, NMR spectra and Raman spectra, and modifiable reflectance properties.

The use of particulate labels to investigate spatial relationships among individual cellular components is described in U.S. Pat. No. 6,642,062, incorporated herein by reference. As described in this patent, individual particles coupled to reagents specific for various cellular components can be prepared in a multiplicity of distinguishable "hues" which are detectable by microscopy and can provide a picture of the spatial arrangement of intracellular components and organelles. Further, as described in U.S. Pat. No. 6,673,554, the changes in spatial arrangement of these components in response to stimuli may be used to evaluate the toxicity of compounds and to identify treatment protocols for disease conditions. The present invention, in one embodiment, relates specifically to the application of these techniques to clinical biopsy samples using these and additional techniques which rely on the sensitivity and multivariant nature of particulate labeling. Certain improvements in particulate labels themselves are also described.

The identity of the particulate labels can be assessed, e.g., for fluorescent labels with a suitable excitation light source and emission filters able to detect wavelengths from the blue to the near infrared, microscopically to determine the position or presence of a single particulate label. Therefore, multiple antigen-antibody complexes, or other biospecific pairs, can be distinguished in a sample by the unique emission properties of each particulate label, enabling multiple parallel assays to be run at the same time in the same physical chamber. In addition, due to the high detectability of particulate labels, as compared to conventional dye molecules, sequencing reactions and the like can be run even when available sample size is too small for conventional analysis. Thus the present invention provides for a more sensitive and more versatile approach to detect the presence of proteins, nucleic acids and the like in a sample or samples. Specific innovative uses of particulate labels are disclosed relating to particular types of multiplexed biospecific interactions. Certain of these assays, whose development was prompted by the availability of convenient particulate labels, are novel in their own right. Although particulate labels provide a preferred embodiment, the use of particulate labels is not a strict requirement for such assays.

Assays of clinical interest are also provided. It is well understood that the cost of bringing a new drug to market is now of the order of $800,000,000, a number driven by the high failure rate of drug candidates. Most of this failure rate is attributable to the reliance by the industry on animal studies in preclinical trials; the transition from results in animals to results in humans is not marked by a one-to-one correspondence. It would therefore represent a step forward to utilize biopsied human tissue samples to assess disease conditions and efficacy of drugs. The present invention facilitates the use of such samples.

DISCLOSURE OF THE INVENTION

The invention provides improved methods to interrogate single cells using microscopy. By employing the methods of the present invention, profiles of the compositions of individual cells may readily be obtained and, in some embodiments, compared to those of other cells. Particular applications of such interrogation include obtaining results in clinical situations and in evaluating protocols for treatment. The methods also permit identification of single cells with desired characteristics, wherein the cells may be further manipulated such as altering their genetic component or immortalizing them. In the improved methods of the invention, it is generally possible to maintain viability of the single cell being interrogated and to retrieve it for further manipulation if desired.

In one aspect, the invention is directed to a method to obtain a sample that may be used in characterizing a subset of components of an individual cell, which method comprises supporting said cell on a permeable membrane support, said support having been overlaid on a sample surface, and allowing cellular components to penetrate the membrane and be deposited on the sample surface.

The membrane supporting the cell (or supporting the residue thereof which does not permeate the membrane) may then be removed from the sample surface and retained. Typically, in this method, a multiplicity of single cells is supported in a pattern on the membrane which has been overlaid on at least one said sample surface. When the membrane is lifted containing the cell or remainder of the cellular components that do not permeate, the arrangement on the membrane corresponds to that of the sample surfaces so that the results from an individual sample surface may be correlated to result from particular single cells. The sample surfaces are examined microscopically to determine their contents and characteristics and the data associated with each cell noted or recorded.

Depending on the information sought to be gained, the cell or cells may simply be permitted to secrete proteins and the composition of the mixture of secreted proteins determined. Alternatively, the cell or cells may be disrupted and their intracellular contents included in the sample surface to be tested. A particularly useful application of the former embodiment is to provide information as to the nature of immunoglobulins secreted by the cell.

The foregoing embodiment may also be employed to test the effects of a drug or protocol on cells as measured by changes in the profile of components measured in the assay.

In another aspect, the invention is directed to a method to obtain a multiplexed characterization of single cell components which method comprises providing a sample of such components with a multiplicity of particulate labels, each displaying a different hue and further comprising a reagent which is a specific binding partner for a particular cellular component. As the particulate labels can be identified individually using a wide field or confocal microscope, numbers of individual particulate labels associated with each component can be determined. The resultant profile may be represented computationally by representing a multiplicity of data points—one data point for each of n components evaluated plotted in n-dimensional space—thus providing a vector in such space for each cell. The vector for each cell is then projected in three-dimensional space to provide a visible/comprehensive characteristic position. In this aspect, as well, the assay may be adapted to demonstrate the influence of a drug, protocol or other external stimulus, such as a toxin on the profile of cellular components.

In still another aspect, the invention is directed to an improved method to obtain immortalized cells that secrete desired immunoglobulins. In this method, because of the sensitivity obtainable, individual B-cells isolated directly from spleen, peripheral blood or lymph nodes, including mucosal-associated lymphatic tissue, can be tested individually for secretion of desired antibodies. Because the assay can be multiplexed, high throughput assays are practical to retrieve cells not only that provide desired antigen recognition, but also that bind specifically to one or more of a variety of epitopes of a single desired antigen, and/or to retrieve a multiplicity of cells that bind a multiplicity of antigens. In this method, a particulate label which is immunoreactive with antibodies in general may be used as a control if desired and the number of particulate labels that bind to these generic antibodies compared to the number of labels that bind antibodies immunoreactive with the desired antigen or epitope. In general, cells may be screened for antigen independent properties such as isotype. In this way, the affinity of the antibodies secreted by particular cells can be rank ordered. This is a significant advance over conventional assays in which weak affinity at high secretion rate is not distinguishable from strong affinity at low secretion rate.

Many of the foregoing methods are applicable in clinical contexts, and in assays to evaluate therapeutic protocols, and the invention includes these applications of the invention methods.

In an additional specific aspect, the invention is directed to a method of evaluating drug performance by evaluating the profile of the T-cell population. Other indicators can also be used to characterize disease states, including translocation patterns, cell surface antigen staining, and the like. Thus, T-cells and tumor cells, for example, can be characterized by their surface antigen pattern which pattern may be elucidated by the use of the particulate labels of the invention. Intracellular translocation may also be used as an indicator.

In another aspect, the invention is directed to a particular type of particulate label wherein a relatively large particle assigned a particular hue by a combination of signal-generating entities is coated with a defined number of smaller particles each with its own distinctive hue. Because microscopy can distinguish sizes, such tandem particles permit a great expansion of multiplexing as will be described below.

In still other aspects, the invention is directed to methods to examine tissues histologically using the multiplexed labels of the invention, and to determine the nature of growth factors that influence embryonic development. In still other aspects, the invention is directed to methods that are advantageous to analyze soluble biological samples that have been subjected to chromatography or electrophoresis. Because of the multiplexed nature of the assays, multiplicities of components can be determined in a single migration lane. For example, sizing ladders may be included within the same lane in which components of biological samples are to be tested.

In another aspect, the invention is directed to an improved apparatus and method for removing a membrane from the sample surface, whereby an aperture adjacent to the surface prevents suction from creating turbulence in the upper portion of the membrane.

BRIEF DESCRIPTION OF THE DRAWINGS

FIGS. 1A-1C are diagrammatic representations of the expanded multiplexing offered by association of tandem particles of different sizes.

FIG. 2 is a photomicrograph of one such tandem particle.

MODES OF CARRYING OUT THE INVENTION

Figure 3:
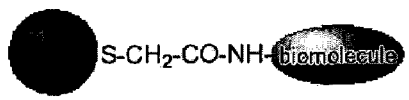
FIG. 3 is a schematic illustration of bioconjugation methods for linking a particulate label with a biomolecule.
Figure 3:
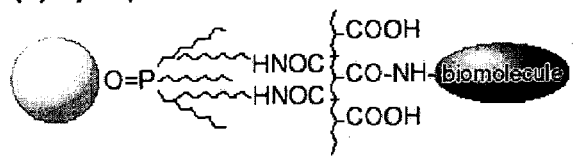
Figure 3:
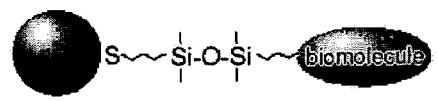
Figure 3:
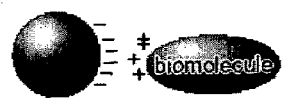
Figure 3:
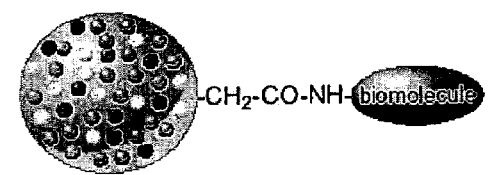

Some of the assays of the invention utilize particulate labels and microscopic observation techniques to phenotype individual cells based on the cell's constellation of surface antigens, intracellular antigens, and/or secreted proteins. Such assays include: characterization of the multivariate cytokine secretion profile of single cells under various conditions; characterization of the specificity and other properties (such as isotype) of secreted immunoglobulins against one another or a panel of antigens; characterization of the tissue milieu associated with patterned tissue growth, including angiogenesis and regeneration; automated pathology in which multiple cell types are individually recognizable by virtue of binding cell type specific antibodies coupled to distinguishable particulate labels or by physical entrapment of the labels (tissue paints); characterization of subcellular localization of proteins; characterization of mRNA expression at single cell level; characterization of protein, nucleic acid, carbohydrate or lipid content of disrupted cells, in situ or spotted in a microarray or following chromatographic or electrophoretic fractionation; characterization of the affinity of a biospecific interaction for a test pair as compared to internal positive controls.

Although certain of these assays are known in the literature, and have been subjected to multiplexed analysis by other means, the utility of conducting such assays using particulate labels has not been previously described. The use of submicron particulate labels requires a sophisticated image analysis system. Surprisingly, the number of particles needed to give a reliable result in the assay is small enough to be accommodated by the field of view of a microscope able to image individual particles. The experiments described herein establish for the first time the feasibility of conducting such assays. For example, in the footprint of a cell secreting an antibody, a typical particle count for one field of view is 500 particles (300 nm diameter) with a background of 10-50 particles and a maximum of ~3,000 particles that can still be resolved, providing one and a half log units of dynamic range. With particles of 5 μm diameter, the footprint of a single cell could only accommodate 1 particle which is not sufficient for these assays. As particle size (and therefore intensity) goes down, however, the feasibility of detecting individual particles in order to define their hue becomes more difficult. In short, the availability of previously described multiplexing reagents, useful for bulk fluorescence measurements or measurements over a large field of view (e.g., a DNA chip position measuring 100 μm or more on a side), does not permit assays on the spatial scale of the present invention (comparable to the diameter of single biological cells).

For some of these assays, e.g., assay of secreted proteins, it is advantageous to interpose a porous membrane between the cells and the assay surface. The cells can thereby be removed and the "footprint" analyzed. Cells of interest, such as B-lymphocytes secreting a desired antibody, can be identified by their footprints and then recovered from the corresponding location on the membrane. This aspect of the invention represents a departure from traditional membrane based assays (filter lifts, Western and Southern blots and the like), and is independent of the use of particulate labels for the analysis of the footprint.

This aspect may further be improved by measures that secure the cells to their defined location on the membrane but do not disturb viability of the cells. Thus, in one embodiment, the cells are deposited on the upper surface of the membrane in the presence of a matrix-forming material, such as methylcellulose. When downward pressure is exerted on the membrane, such as through centrifugation, the cells migrate through the semisolid matrix and are held in place at the surface of the membrane. While methylcellulose is exemplified, any polymer whose behavior is similar may be substituted—i.e., polymers that become more rigid, e.g., on cooling, pH change or when a moderate downward pressure is exerted. Further, the integrity of the accumulation of cellular components on the sample surface may be improved by adding a binding partner for the relevant component to the matrix material either simply by mixing or by coupling the binding partner covalently to the material that forms the matrix. For example, if the component to be assessed on the sample surface is an immunoglobulin, protein A may be used as the binding partner. In a modification of this approach, an additional matrix containing binding partner, such as a dextran matrix, may be superimposed on the upper surface of the membrane containing the sample cells. This feature reduces the background of the assay.

Figure 11:
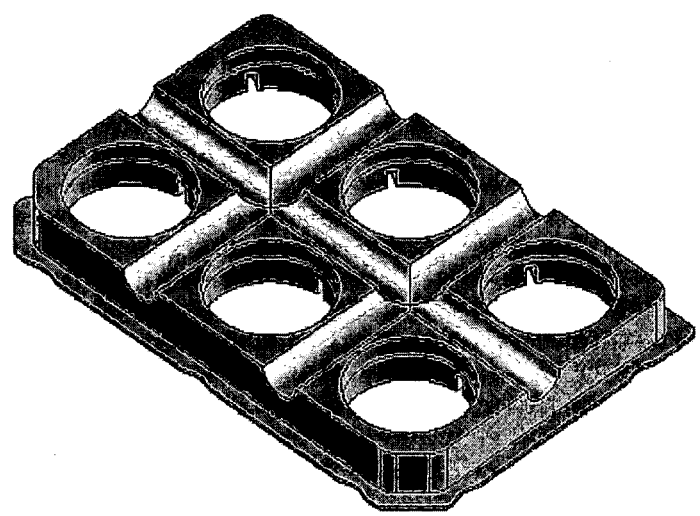
FIG. 11 shows one embodiment of an improved method for lifting a membrane from a sample surface. As shown, an aperture directly above the sample surface prevents suction from creating turbulence at the upper surface of the membrane to be removed.

In this assay, further improvements can be realized by providing an apparatus which is constructed so as to prevent turbulence from occurring at the upper surface of the membrane when it is removed from the sample surface. This can be accomplished by employing an aperture adjacent the sample surface to prevent suction from creating this turbulence. This is illustrated in FIG. 11.

In general, assays which examine cellular parameters, such as secreted proteins, intracellular components, cell surface markers, and the like, which take advantage of the multiplexing capability of the particulate labels and the ability to measure these parameters in a single cell, can be performed either using the membrane-based technology described above or can be conducted simply on a surface in which the cell is embedded or otherwise associated. By using microscopic observation and the particulate labels of the invention, multiple cellular components can be enumerated and identified in a single assay. This is particularly usefull in determining the effects of an external stimulus, such as a drug, on the interrogated cell. In such assays, a control cell that has not been subjected to the external stimulus is interrogated and the profile of components compared to that obtained from a cell that has been treated with the external stimulus. The comparison of the profiles elucidates the nature of the cellular response to the stimulus. In one embodiment, where the stimulus is a drug, dose response curves may be obtained by exposing individual cells to various levels of drug and comparing each level to the control. Such assays may be performed on a variety of animal tissues, including human tissues where evaluating individual response to particular drugs or protocols is important.

The present invention is also directed to methods of using particulate labels coupled to biospecific probes in bioanalyte detection. The particulate labels are individually detectable and distinguishable and can be located in spatial relationship to each other, if desired. Particulate labels can be used as nonradioactive biolabels by linking a biorecognition moiety, such as proteins, antibodies, ddNTP's, primers, or markers, etc., to the particulate label. The paradigmatic particulate label is a latex particle impregnated with organic dye fluors, as described in U.S. Pat. No. 6,492,125 incorporated herein by reference; other particulate labels, e.g., those that employ quantum dots, may also be used as further described below. Particulate labels can also be constructed using detectable properties other than fluorescence, such as phosphorescence, electrochemical luminescence, as well as NMR or Raman signals. Further, self-assembled dendrimers can create in situ an object equivalent to such pre-assembled particulate labels. As described below, the particulate label may also be comprised of a relatively large particle to which a multiplicity of smaller particles are bound to the surface, wherein each of the smaller particles has, itself, a distinct hue.

The optical properties of particulate labels are ideal for multiplexing, as two or more individual signal generating moieties may be used at various ratios to generate a multiplicity of hues. The number of signal generating moieties may be expanded as desired. For example, ten intensity levels at each of six colors could theoretically code for one million nucleic acid or protein sequences. Particulate labels that are in the size range of 10-300 nm have dimensional similarity with biological macromolecules (e.g., nucleic acids, proteins, and protein complexes such as ribosomes or viruses). This similarity allows improved integration of the nanomaterials with biological molecules, as compared to the much larger combinatorially colored particles (5-50 μm) known in the literature, although these larger particles may also be used in some aspects of the invention. The smaller particles have advantages in immunoassays, medical diagnostics, targeted therapeutics, and high-throughput drug screening when used as tags for diffusible reagents whose final location provides the assay readout. This is in contrast to assays described, for example, in U.S. Pat. No. 6,492,125 where particles with characteristic labels are used to identify particular analytes and the quantity of the analyte is determined by an independent label attached to the analyte itself. While some applications of the invention method have been previously described using multiplexed labels, the use of particulate labels in assays based on counting individual particles, as contrasted to integrating intensity from a population, is permitted by the ability to detect individual particles microscopically.

Further enhancement of multiplexing can be obtained by virtue of the ability of microscopic techniques to discern size in addition to hue. A particularly advantageous embodiment of this concept is illustrated in FIGS. 1A-C. As shown, by way of illustration, a set of four fluorophores may conveniently be used in various combinations to generate 20 hues on particles of relatively small size, e.g., 10-100 nm, typically 50-100 nm. Thus, 20 such particles provide 20 distinct labels. Larger particles, for example, 200-500 nm in diameter can similarly be coded with, if desired, the same four fluorophores to generate another set of particles with 20 hues, as shown in FIG. 1B. If the particles of FIG. 1A and FIG. 1B are used together in an assay, a total of 40 distinguishable particles will be available—20 hues in two sizes. By adsorbing or covalently coupling the smaller particles to the surface of the larger, as shown in FIG. 1C, a multiplicity of 20×20 or 400 "tandem" particles with distinct hues is provided. If an assay readout requires proximity of two such particles, 400×400=160,000 distinguishable assays can be conducted (e.g., suitable for genomic scale DNA assays).

The smaller particles may be adhered to the larger ones through a variety of linking techniques known in the art, for example, by providing each particle with a reactive group and supplying a bifunctional linker. Alternatively, the smaller particles may be provided with a substituent containing an amino group while the larger particles comprise substituents with carboxyl groups; formation of an amide linkage would then result in the desired coupling. Alternatively, the small particle might be provided a covalently linked biotin and the larger particle a covalently linked avidin wherein the biotin/avidin interaction provides the desired linkage. A wide variety of methods to link these particles is available in the art.

Particles of this type have been successfully prepared. FIG. 2 shows a photomicrograph of the embodiment shown in FIG. 1C.

The tandem particles can be made more complex by increasing the number of sizes associated with a single particulate label. For example, a large particle of, for example, 1-50 μm, preferably about 10 μm, might have attached to its surface or embedded within it intermediate size particles of, e.g., 500 nm-800 nm and additional, even smaller particles of about 100-200 nm. By providing each of the smaller and middle size particles with a distinctive hue, the multiplexing of the tandem particle is further increased.

Such tandem particles may be prepared by a variety of means including inkjet printing wherein the smaller particles are suspended in a polymer that is expanded to create the larger host particle. Alternatively, the largest particle may be assembled to about half its final size and then the smaller particles added in a manner that causes them to stick to the surface followed by resumption of polymerization. Still a third way to prepare these complex tandem particles is to swell the largest particle in an organic solvent so that the smaller ones can diffuse inside. In still another approach, a "smart" polymer may be used—i.e., one that undergoes a sharp phase transition as a function of conditions such as temperature and pH to alter the permeability of the largest particle so as to admit the smaller ones.

In one application, the invention applies to profiling a multiplicity of cellular components, whether intracellular, surface displayed, or secreted. In these aspects, the invention is directed to labeling the desired multiplicity of cellular components with the particulate labels described above having a biorecognition moiety coupled to the distinguishable particle, the biorecognition moieties selected for the desired components. The selected proteins can be the cytokine secretion pattern of single T-cells, for example. The method may also be used to identify single B-cells or hybridoma colonies that secrete immunoglobulins of the desired specificity and affinity. In another specific application, the biorecognition moieties are selected so as to interact with HLA proteins displayed on the surface of the cell. Other specific applications include the determination of a number of reporter genes which can be expressed as secreted proteins or determined upon lysis of the cell. A multiplicity of effects of factors that regulate gene expression can thus be determined simultaneously. Similarly, the profiling methods of the invention are applicable to all types of cells, including yeast, bacteria, plant cells and the like.

In still another application, the methods of the invention may be used to "paint" histological samples with a granular label, i.e., the multihued particulate labels useful in the invention. A granular label is more readily visualized than standard histological dyes. Imaging of this type is also useful in vivo.

The particulate labels may also be used in capillary electrophoretic analysis, such as DNA sequencing reactions, and in mutation-detection analysis methods, such as single-strand conformation polymorphism (SSCP), allowing for the detection of nucleic acids and amino acid mutations with increased sensitivity, because of the enhanced sensitivity in the ability to detect single particles microscopically. Thus, the presence of an analyte in a sample may be detected using chromatography in conjunction with Western (antibody), Southern (DNA) and Northern (mRNA) analysis, optionally employing transfer to a filter which is then probed. In such applications, the multiplexing capacity of particulate labels allows for multiple analytes present in a substance to be analyzed at the same time, in the same lane of the sorbent. The presence of at least one analyte in a solubilized biological sample can be detected by separating components of said solubilized biological sample by chromatography or electrophoresis, said components being labeled before or after separation with a particulate label; and detecting a signal such as fluorescent emission using a microscope from the particulate label indicating the presence of the analyte. The soluble components can also be analyzed following diffusion through a membrane and capture on an underlying surface as described above. The footprint of individual cells, either intact or disrupted, can be analyzed; likewise, the insoluble components that are retained by the membrane can also be analyzed.

The following terms may be defined to clarify the invention: "A", "an" and "any" are each intended to include both the singular and plural forms.

The invention employs, as means to associate the particulate labels with individual analytes, "specific binding partners" for the analytes. Common forms of specific binding partners are antibodies or immunoglobulins. The classical "antibody" specific for a particular antigen is obtained through immunization of a suitable vertebrate and recovery of polyclonal antibodies from the plasma or serum or recovery of monoclonal antibodies through hybridoma or recombinant technology. It is well known that antibodies as obtained in this way are not required in their entirety for binding specificity; only the variable regions need be present. Thus, included within the term "antibodies" as used herein, are fragments of the antibodies such as $F_{ab}$, and $F_{ab'}$, fragments. In addition, the availability of recombinant techniques makes possible altered and species-adapted forms of specifically binding regions, such as single-chain $F_v$ "antibodies." "Specific binding partners" also include proteins in general that can contain a variable binding region. A solvent-exposed loop in such proteins can be altered using mutagenic techniques to afford a wide variety of binding specificities (Napolitano, E. W., et al., *Chem. & Biol.* (1996) 3:359-367). Also included in this category of specific binding agents are miniproteins, such as the variants of avian pancreatic peptide described by Schepartz and colleagues (WO 01/81375). In addition to proteins, oligonucleotides of differing binding specificities can be generated, e.g., by the Selex technique (U.S. Pat. No. 5,567,588). Other specific binding partners include ligands and their corresponding receptors, avidin/biotin, and any other moiety that can interact specifically with an opposite member.

"Fluorescence" is the emission of light resulting from the absorption of radiation at one wavelength (excitation) followed by nearly immediate re-radiation usually at a different wavelength (emission). Organic fluorescent dyes are typically used in this context. "Luminescence" refers to the process of emitting electromagnetic radiation (light) from an object. Luminescence results from a system which is "relaxing" from an excited state to a lower state with a corresponding release of energy in the form of a photon. These states can be electronic, vibronic, rotational, or any combination of the three. The transition responsible for luminescence can be stimulated through the release of energy stored in the system chemically or added to the system from an external source. The external source of energy can be of a variety of types including chemical, thermal, electrical, magnetic, electromagnetic, physical or any other type capable of causing a system to be excited into a state higher than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy X-ray radiation. Typically, luminescence refers to photons in the range from UV to IR radiation.

A "biological sample" refers to cellular components, such as DNA or RNA, a sample of isolated cells, tissue or fluid, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

The word "footprint" as used in the context of the assays herein has a specific meaning. It is the collection of moieties on a sample surface that has accumulated a complement of components associated with a single cell or defined clone, so as to provide a profile of the components of the cell (including secreted components) or of a subset thereof. In a preferred embodiment, the complement of components has been filtered through a permeable membrane from the single cell or defined clone. Thus, in one method of the invention, cells are supported individually or in defined clones on a permeable membrane and a footprint collected beneath them on the sample surface. Mixtures of cells may also be used to generate a footprint which then characterizes the mixture rather than a single cell.

"Particulate label" refers to a particle of typically nanometer dimensions, e.g., 5-800 nm, 10-500 nm or about 50-200 nm to which may be bound a biorecognition moiety (i.e., a specific binding partner for an analyte) and which is detectable through emission of signal, typically, but not necessarily, emission of light. A preferred size is ~300 nm. The particulate label will have a "hue" which is defined as its characteristic signal. As described herein, its characteristic signal or "hue" is, in some cases, generated by a multiplicity, typically 2-4 or more signal generating moieties present on the particle at specific ratios. Fluorophores are typically used to generate signals. Quantum dots may also be used. When quantum dots are used, because they have very sharp emission peaks, a single quantum dot may be sufficient to constitute the particulate label optionally bound to a biorecognition moiety, which then has the characteristic hue of that quantum dot.

FIG. 3 shows a comparison of (a) the excitation and (b) the emission profiles between a previously used organic dye rhodamine 6G and CdSe quantum dots. The quantum dot emission spectrum is nearly symmetric and much narrower in peak width. Its excitation profile is broad and continuous. By contrast, the organic dye rhodamine 6G has a broad and asymmetric emission peak and is excited only in a narrow wavelength range. By varying the size and composition of quantum dots, the emission wavelength can be tuned from the blue to the near infrared. Despite these differences, the same filter set can be used to read either fluor. In principle, the narrower emission profile of the CdSe label should allow making a family of such labels, each a slightly different size, and thus emitting a slightly different wavelength. In practice, the ability to achieve tight size distribution during manufacture limits the diversity of types.

Alternatively, particles with more complex hues may be constructed using quantum dots as the signaling means. In these methods, a larger particle, typically on the order of 1-5 μm, is associated with a specific ratio of 2, 3 or 4 quantum dots, thus enhancing the number of alternative hues available. These larger particles are in some contexts troublesome because of their size; the resolution required in most biological samples is sufficiently fine-grained that in some methods a 5 μm particle is disadvantageous.

For very small particulate labels in a particular set it may also be advantageous to have a uniform "clamped value" signaling moiety that is of the same energy and same intensity for all members of the set of particulate labels. This allows the number of particles associated with a particular detection space to be determined even if the resolving power is not sufficient to limit the detection space to the dimensions of a single particle. The nature of these "clamped value" parameters is further described in PCT publication US 2003/031818, incorporated herein by reference.

A "hue characteristic of a labeled component" refers to the hue of the particulate label to which that component is attached. Thus, when a multiplicity of components is labeled with a multiplicity of particulate labels, by pairing a particular component with a particular particulate label, the component assumes the characteristic hue associated with the particulate label.

Thus, the term "particulate label" may be used in two contexts: in one case, the label is the particle itself that emits a characteristic signal or collection of signals to give a characteristic hue where the label itself is said to be attached to a reagent or biorecognition moiety. In the other context, the "particulate label" further includes the biorecognition moiety as it is used to label an additional component to which the biorecognition moiety is specifically bound.

The particulate labels useful in the invention can be of some variety. In one embodiment, these are nanoscale latex spheres wherein the hue can be adjusted by varying the ratio of impregnated organic dye fluors. Latex and similar particles coupled to combinations of signal generating moieties, especially fluorophores to generate a multiplicity of hues and coupling of these particles to biorecognition molecules is described in detail in U.S. Pat. Nos. 6,642,062 and 6,492,125 cited above. A very large number of possible hues can be generated by using the types of particulate labels described above, wherein a multiplicity of smaller particles each with a distinctive hue is distributed on the surface of a larger particulate with its own hue.

In other embodiments, luminescent quantum dot labels may be used wherein the emission of the label can be adjusted according to the size and material composition of the quantum dot. Semiconductor quantum dots may be coupled to biorecognition molecules. Although these nanometer-sized conjugates are generally not water-soluble, they can be suitably modified to improve solubility and biocompatibility. Metal and semiconductor nanoparticles are available in the 1-10 nm size range, and may be linked to biomolecules such as peptides, proteins and DNA. Analogous particulate labels where a signal generating moiety emits distinguishable signals other than fluorescence, including phosphorescence, reflectance, electrochemical luminescence, as well as NMR or Raman signals may be used. Self-assembled dendrimers that create in situ an object equivalent to particulate labels may be used rather than, e.g., latex particles.

Particulate labels may be smaller than the minimum wavelength of visible light (i.e., their detection depends on the signals they emit, not on imaging in the conventional passive sense, including phase contrast or absorption), must be "bright" enough (i.e., detectable enough) for single particles to be counted microscopically, as contrasted with integrating total intensity arising from a population of particles, and should, in some applications, be available in at least 5, and preferably at least 10 distinguishable types.

With respect to embodiments that employ quantum dots, these substances are typically composed of atoms from periodic table groups II and VI (or III and V), and are defined as particles with physical dimensions smaller than the exciton Bohr radius. For spherical CdSe particles, this occurs when the particle diameter is less than ~10 nm. Use of group IV atoms, such as silicon, has enabled a simpler chemistry for conjugation to carbon containing moieties; further, oxidation of carbon containing moieties to yield charged moieties simplifies creation of water soluble forms. Both group II-VI (e.g., CdSe, CdTe, CdS, and ZnSe) and group III-V (e.g., InP and InAs) nanocrystals have been synthesized and studied extensively.

Morphologically, quantum dots are not smooth spherical particles, but are faceted with many planes and edges. Reduced aggregation and precipitation of the solubilized quantum dots by using chemically modified proteins to coat and "passivate" the surface has been accomplished. The protein layer provides multiple functional groups (amines, carboxylic acids, and cysteine residues) for covalent conjugation with biospecific probes.

Figure 4:
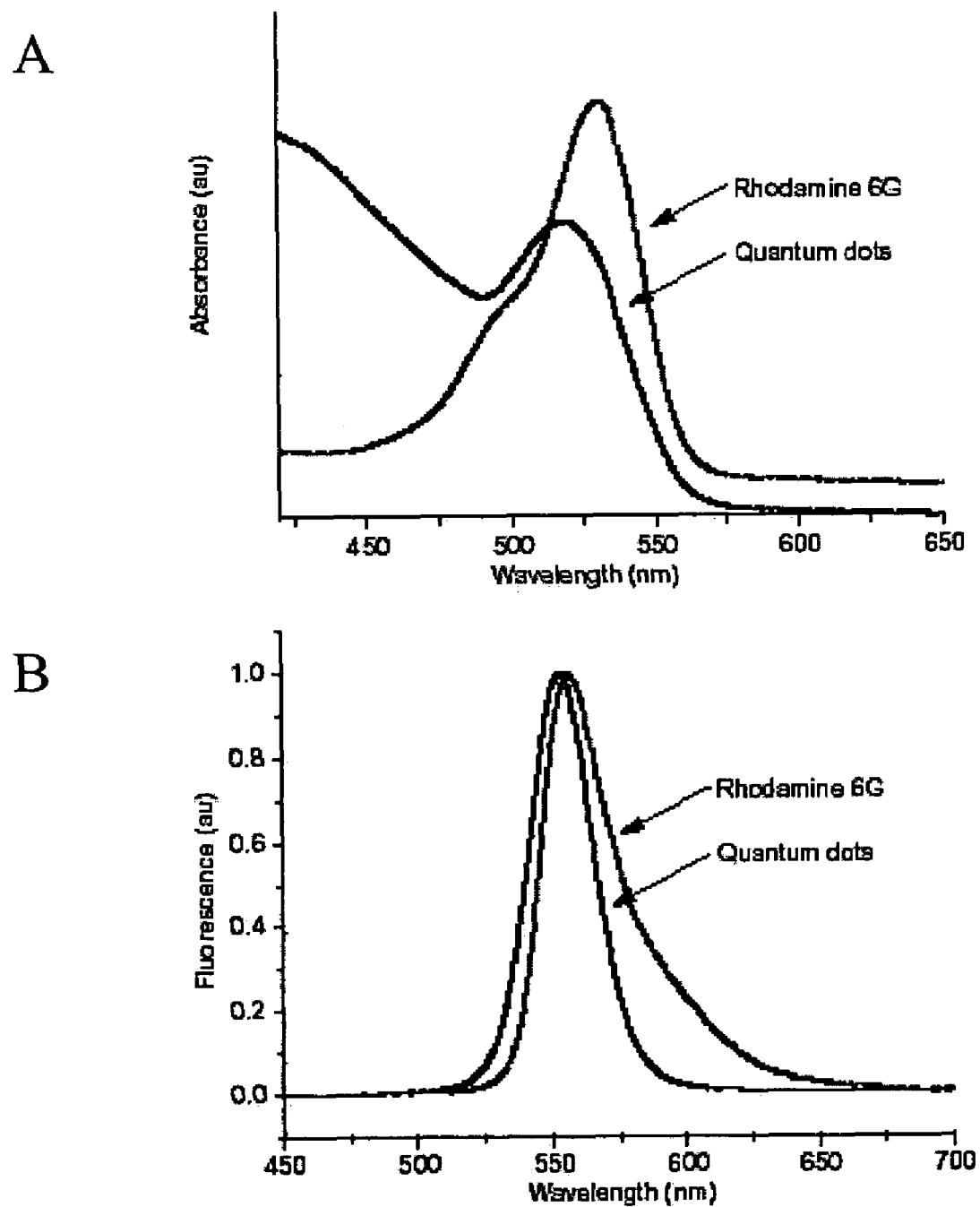
FIG. 4 shows a comparison of (a) the excitation and (b) the emission profiles of the organic dye rhodamine 6G and CdSe particulate labels. Similar filter sets are useable to measure either.

Conjugation of biospecific probes to quantum dots can be accomplished by numerous methods that are well known in the art of biospecific binding assays, schematically illustrated in FIG. 4. Reactive functional groups include primary amines, carboxylic acids, alcohols, and thiols. Water soluble quantum dots carrying one of these moieties may be derivatized by known methods. Because the surface area of a single quantum dot is large, two to five protein molecules and fifty .or more small molecules (such as oligonucleotides or peptides) may be conjugated to a single, e.g., 4 nm, quantum dot. Examples of bioconjugation methods for linking a quantum dot with a biomolecule include: (a) use of a bifunctional ligand such as mercaptoacetic acid (Chan, W. C. W., et al., Science (1998) 281:2016-2018); (b) TOPO-capped quantum dots bound to a modified acrylic acid polymer by hydrophobic forces; (c) use of a mercaptosilane compound (Bruchez, M., Jr., et al., Science (1998) 281:2013-2015); (d) linking positively charged biomolecules to negatively charged quantum dots by electrostatic attraction (Mattoussi, H., et al., J. Am. Chem. Soc. (2000) 122:12142-12150); and (e) incorporation of quantum dots in microparticles and nanoparticles which have reactive groups (Han, M. Y., et al., Nat. Biotechnol. (2001) 19:631-635).

Although, a single quantum dot is ~20 times as bright as a single organic dye molecule, such as rhodamine or fluorescein, quantum dots are 5-10 times the size of a dye molecule, and the increased signal can be mimicked by larger dyes. Bawendi and coworkers (Murray, C. B., et al., J. Am. Chem. Soc. (1993) 115:8706-8715 and Dabbousi, B. O., et al., J. Phys. Chem. B. (1997) 101:9463-9475) estimated that the molar extinction coefficients of CdSe quantum dots are similar to the absorption cross-sections of phycoerythrin, a multichromophore fluorescent protein. In practice, the previously disclosed latex particles impregnated with dyes are of comparable brightness, and allow creation of even larger numbers of distinguishable objects than quantum dot technology affords using readily available manufacturing techniques.

Signal generating moieties that emit light, whether organic dyes, luminescent materials, or quantum dots can be detected by standard detectors which can sense the intensity of light of particular wavelengths or wavelength ranges, including photomultiplier tubes or photographic film. That is, the emitted light from quantum dots is unremarkable as compared to light emitted from standard fluors. Preferred commercially available detectors are charge coupled devices (CCD's) equipped with standard color filters, as used in wide field or confocal fluorescence microscopes, instruments which provide high resolution in three spatial dimensions, multiple color dimensions, and which can be adapted to provide high time resolution as well. Commercial suppliers include Applied Precision (Seattle, Wash.) with many pioneering publications authored by a group headed by John W. Sedat. These publications include Urata, Y., et al., J. Cell Microbiol. (1995) 131:279-295; Paddy, M. R., et al., J Cell Sci. (1996) 109:591-607; Chen, H., et al., J. Structural Biol. (1996) 116:56-60; and Kam, Z., et al., BioImaging (1997) 5:40-49. In addition, a summary of these techniques is provided in a chapter by Swedlow, J. R., et al., in "Deconvolution of Images in Spectra", Second Edition, (1997) Academic Press, pages 286-307.

The assay modalities set forth below illustrate a number of the invention features. The first four modalities illustrate various applications of the ability to characterize the components of single cells or defined mixtures of cells. Applications of such an ability include clinical studies, for example, by analyzing cytokine profiles of T-cells, improvements in obtaining suitable cells for the preparation of monoclonal antibodies, analysis of cell surface markers, and use of these assays to test the effectiveness of protocols or to identify cells that have unusual phenotypic characteristics. While obtaining cytokine profiles and testing for secretion of antibodies of particular specificities are illustrated, the assays of the invention are also useful for a variety of cellular components, including reporter proteins that may most conveniently be expressed as secreted proteins in response to regulators of gene expression. Thus, the influence of a multiplicity of expression regulators may be examined at the same time. In addition, the methods are applicable not only to vertebrate cells, but any cells, including bacteria, fungi, plants and the like. For bacteria that have periplasmic space, cell walls may be ruptured during the assay and the contents of the periplasmic space examined according to the method of the invention. The method is also applicable to determining the variety of components expressed using phage display.

Because of the multiplexed nature of the assays, profiles containing data with respect to three or more cellular components may be obtained simultaneously. Preferably, four, five, ten or more components can be determined in this way.

Some of the assays employ the features of the invention whereby a sample surface footprint is correlated with a cell or combination of cells on a superimposed membrane; other embodiments simply employ cells immobilized on surfaces individually. Some of the individual features of these assays, such as the use of corresponding locations on membranes and sample surfaces are applicable regardless of the nature of the label. However, in many instances, the assays are made practical by use of the particulate labels of the invention. This is the case, for example, in the context of assay modalities 5-7 where the properties of the particulate labels make possible extremely small samples or permit modifications to assays that would not otherwise be obtainable.

Since the particulate labels used in the invention are small, bright and diverse, they are useful in assays that are inherently microscopic in scale, such as single cell analysis, and in assays for which specimen material is limiting or heavily contaminated with numerous interfering analyte types, such as shed tumor cell detection.

Assay Modality 1. Cytokine Profiling of Single T-cells.

In one illustrative assay, particulate labels are used to characterize the proteins secreted from a single cell. The general assay format for secreted proteins is known as ELISPOT (ELISA on a spot). Although the basic technique has been known for decades, some improvements on the ELISPOT assay are described in U.S. Pat. No. 6,410,252 (primarily use of a membrane as capture surface for secreted proteins). ELISPOT assays have previously been designed to determine one or two secreted proteins. First a capture surface is prepared which includes antibodies against the secreted proteins of interest or the surface itself is used as a non-specific capture medium. Since the eventual multiplexing to follow is virtually unlimited when using particulate labels as detection reagents, as many capture antibodies or other specific binding partners as there are secreted proteins of interest in the experiment may be deposited on the well surface. A cell suspension is then deposited in the microplate well. Specific cell stimulants, if needed, may then be added to the well to elicit the cell response of interest. After an incubation period, the wells are washed removing the cells and leaving behind the secreted proteins of interest bound to their respective antibodies on the well surface (the "secretion footprint" of the cell). In the conventional ELISPOT assay, antibody conjugated to a high amplification detection tag, such as alkaline phosphatase or horseradish peroxidase, is used to probe the captured proteins, with subsequent generation of signal by adding enzyme substrate.

The use of particulate labels simplifies and considerably extends this assay. To identify the secreted proteins in the cell surround or footprint, a suspension of particles labeled with a second set of antibodies is added to the well, in a classic "sandwich" assay format (one antigen but two non-overlapping epitopes—a capture antibody recognition site and a detection antibody recognition site). Alternatively, only the particulate labels are coupled to specific binding partners for the antigen, relying on general adhesion properties of the sample surface to retain the antigen/cytokine. Each conjugated characteristically hued particle binds to its respective secreted protein, thus identifying its presence in the secretion footprint of the specific cell that was previously located at the site. Numerous cells within a well can be characterized in an automated way and grouped according to their multiplexed secretion profiles, thus providing a powerful and qualitatively new capability in immunological investigations.

Figure 5:
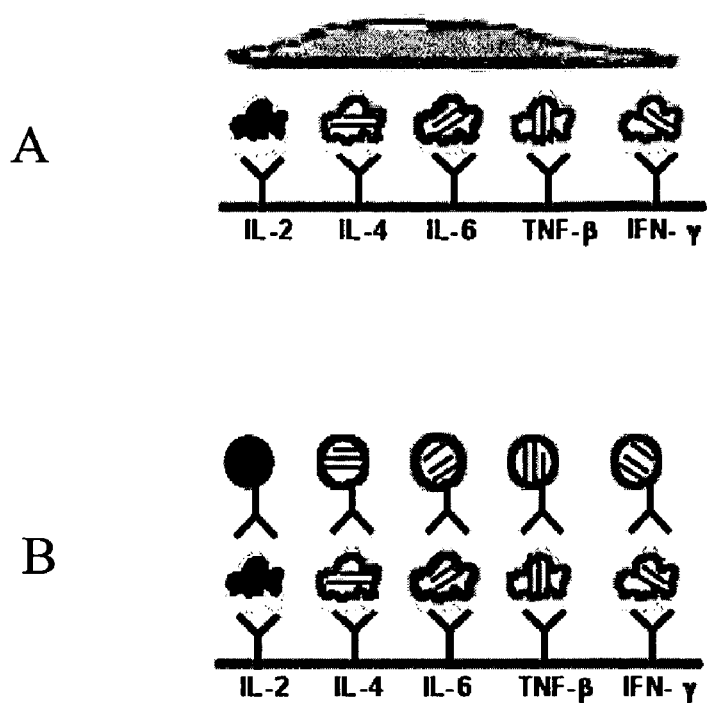
FIGS. 5A and 5B show a schematic of the multiplexed assay employing the multiplexed labels of the invention. In step 1 shown in FIG. 5A, multiple cytokines secreted from a single T-cell are captured on an underlying surface by a mixture of specific capture antibodies; in step 2 shown in FIG. 5B, after removing the cells the captured cytokines are detected using a mixture of specific detection antibodies each coupled to a distinguishable particulate label.

This is illustrated in FIG. 5. In step 1 (FIG. 5A), a single cell is permitted to reside above a collection of antibodies absorbed or otherwise coupled to a solid surface, such as a microtitre plate well. The secreted proteins are bound to their respective antibodies on the surface. After removal of the cell by washing (or if the cell is contained on a membrane, by lifting the membrane), the surface is probed in step 2 (FIG. 5B) with sandwich forming antibodies, each specific for a different cytokine and each labeled with a particulate with a distinguishable hue characteristic of the antibody to which it is bound. The surface is then profiled for the identification of the number and type of individual particles.

Figure 6:
FIG. 6 is a micrograph obtained using a wide field microscope image of IL-2 secreted from a single cell and labeled with the particulate labels of the invention. Each individual particle bound to IL-2 is detectable by virtue of its label.

FIG. 6 shows a photomicrograph of a single cell profiled for its secretion of IL-2. In obtaining this photograph, antibodies immunospecific for IL-2 were first coated on a well surface, a sample sufficiently diluted to provide views of individual cells was added to the well and the well incubated under conditions where IL-2 would be secreted. After washing away the cells, the well was treated with a counterpart anti-IL-2 antibody coupled to a fluorescing particle. As shown, the individual particles are discernable as they radiate from the actual location of the cell itself. At low particle concentration, density of the particles in the center zone is low enough that individual particles can be recognized. With this resolution, three or more cytokines can readily be measured.

Figure 7:
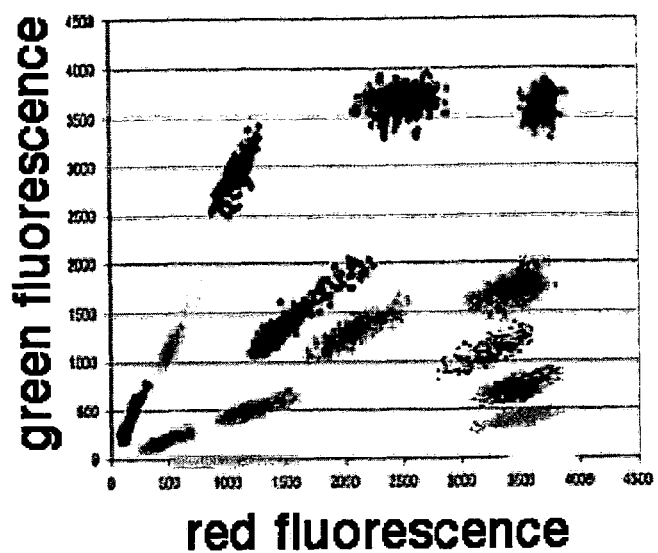
FIG. 7 shows the intensity of each of two color channels for pure particulate labels in a multiplicity of hues. Such multiplicity is useful and sometimes mandatory in the methods of the invention.
Figure 8:
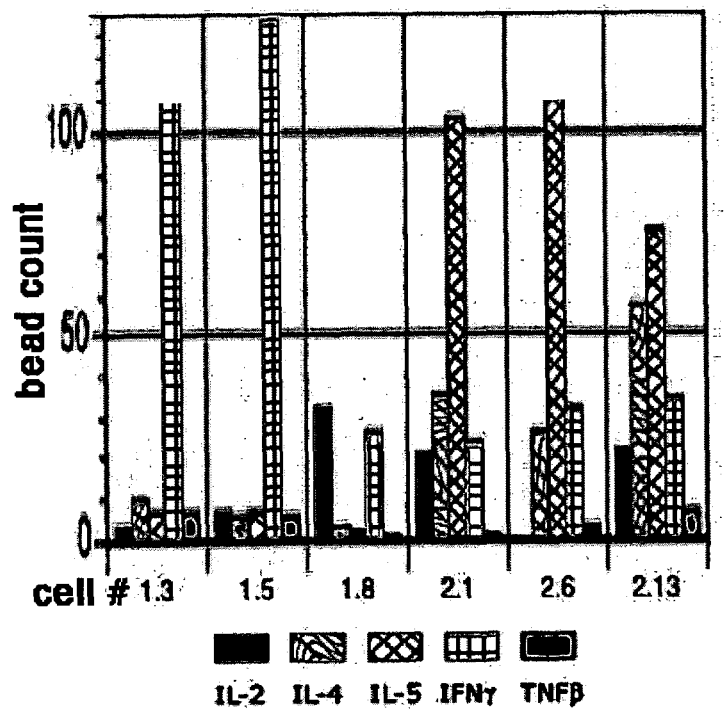
FIG. 8 is a bar graph showing representative 5-cytokine profiles for each of six cells. Decoding of the particulate labels is based on the reference label intensities in two color channels shown in FIG. 7.

As shown diagrammatically in FIGS. 7 and 8, five secreted cytokines are detected simultaneously: IL-2, IFN-gamma, and TNF-beta ($T_H1$ subtype canonical cytokines), and IL-4 and IL-5 ($T_H2$ subtype canonical cytokines). The multihued particles useful in this assay can readily be distinguished as illustrated in FIG. 7. As shown, the hues are created by combination of green and red fluorescence and each type of particle distinguished by the predetermined ratio. The reference hue chart in FIG. 7 shows intensity in each of two color channels for pure particles of each type. More than 5 particle types are fully distinguishable (>98% accuracy). The same protocols that have been used to accomplish this 5-plex assay are readily extendable to higher degrees of multiplexing.

Actual results are shown in FIG. 8. Spleen cells were deposited in a microplate well that had been prepared with a capture surface containing antibodies to each of the 5 cytokines above. The heterogeneous spleen cell mixture was stimulated with a combination of anti-CD3 and anti-CD28 thus eliciting a cytokine secretion response. As shown in FIG. 8, the pattern of cytokine secretion differs among the six cells tested.

Figure 9:
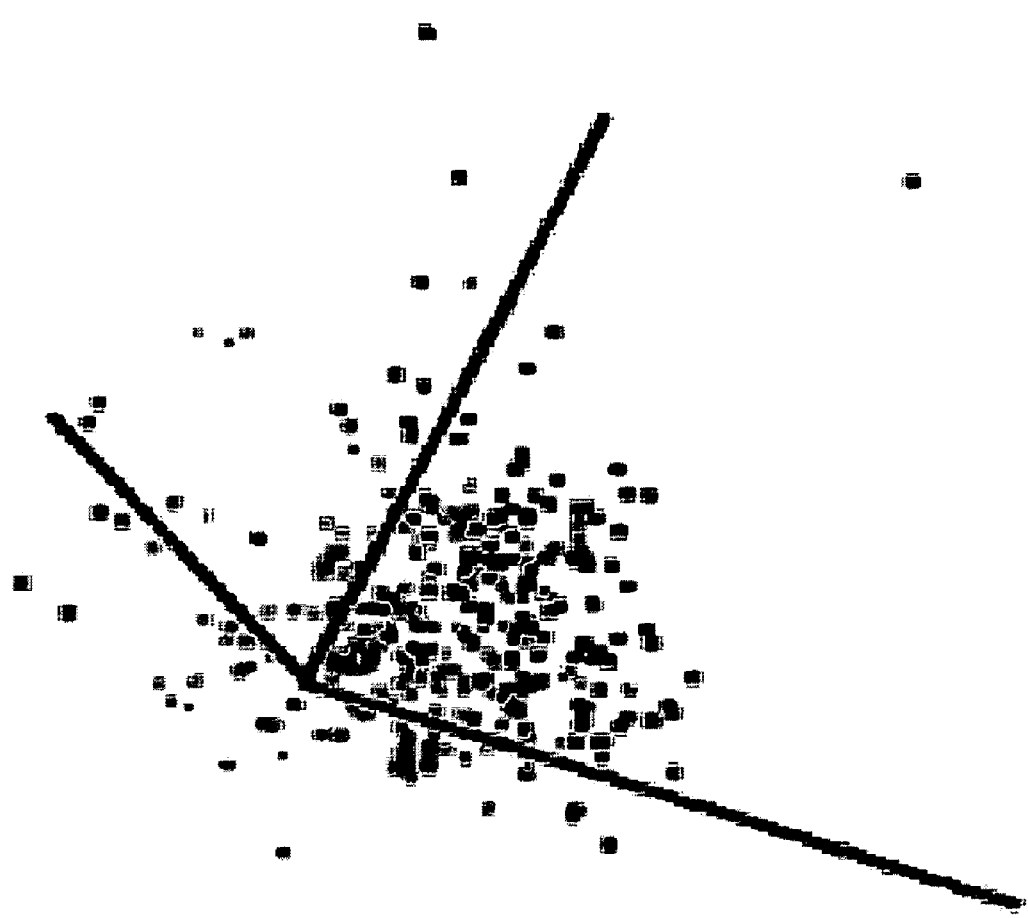
FIG. 9 illustrates the secreted cytokine profiles from a multiplicity of single cells of two murine strains. Each point is a representation of a 5-cytokine profile for a single cell, projected onto the first three principal components of 5-dimensional space. Although both strains show a spectrum of types, the distribution is offset between the two strains with one strain represented by gray and the other by black dots.

FIG. 9 illustrates the cytokine profiles for T-cells from spleens of two murine strains, C57/Black and Balb/C. The cells were stimulated using PMA/ionomycin, following standard immunological protocols, and plated onto a polystyrene surface previously coated with capture antibodies for IFN-gamma, IL-2, IL-4, IL-5 and IL-6, a suite that has been described as containing representatives of either Th1 (IFN-g, IL-2) or Th2 (IL-4, IL-5, IL-6) T-cell subtypes. After incubation overnight, the cells were washed off and the polystyrene surface exposed to detection antibodies for the 5 cytokines, each conjugated to a different particle type. After washing, the areas of high particle density were identified at low magnification and the particles themselves imaged at high magnification in a wide field fluorescent microscope. The number of each particle hue in the "footprint" of each cell was recorded.

For each murine strain, ~1,000 cell footprints were analyzed. The profile of each cell (i.e., the number of particles for each of the 5 cytokine detector particle types) was plotted as a point in a 5-dimensional (5-D) space. The number of particles detecting IL-2 were considered as plotted on the x-axis, the number for the IL-4 type on the y-axis and so forth. Since 5-D space cannot be readily visualized, the resulting data were projected onto the most informative three dimensions, which were determined by applying principal components analysis to the 5-dimensional data set. This is a standard tool of multivariate analysis.

FIG. 9, then, shows the 5-D cell profiles in the reduced 3-dimensional (3-D) space for the two strains (black and gray points respectively). Two conclusions are supported by this analysis. First, the cell phenotypes show a spectrum of types, not two clumps corresponding to Th1 and Th2, contrary to the widely held description of T-cells as falling into two types, Th1 and Th2. Second, the Th1 vs. Th2 paradigm is not entirely false, however. The two murine strains are known to differ in their bias towards Th1 or Th2 response, and indeed the distribution of the cell profiles for the two strains are offset reflecting this bias.

For some applications, it is important to recover the secreting cells following the analysis, not just to document their phenotypes. This property is achieved by plating the colonies onto a membrane and capturing the secreted protein after it passes through the membrane. Surprisingly, the footprint expansion introduced by diffusion through the membrane is tolerable, allowing the captured protein to be related back to the overlying cells. This aspect of the technology provides an opportunity to investigate the effect of a drug on the cytokine secretion profile. A population of T-cells is plated on a membrane and the secreted proteins are captured on a plate underneath the membrane. The membrane is then moved to a new plate, after which the cells are exposed to the drug, and the secreted proteins again captured on the plate. The frequency and character of the changes induced are then recorded. Other perturbants can also be analyzed in this manner, e.g., hormones, other cells, toxins. For example, the perturbant could be a cosmetic whose skin irritancy properties are under investigation, with the T-cell population drawn from test subjects as an alternative to animal testing.

Any array of secreted proteins can be identified and analyzed in this way, not simply cytokines secreted by T-cells. Thus, a variety of paracrine and autocrine factors can be determined by appropriate selection of antibodies or other specific binding partners as biorecognition molecules coupled to the particulate labels. The technique is not limited to mammalian cells, but can be used to investigate the phenotype, including transformed phenotypes of prokaryotic plant, and animal cells in general. It is further not limited to secreted components, but may be applied to other components, according to the treatment of the individual cells.

Assay Modality 2. IgG Profiling of Single B-Cells or Hybridoma Colonies.

IgG secreted from a single B-lymphocyte or hybridoma may also be analyzed using the invention methods. A population of, or individual, B-cell(s) may be screened against many antigens concurrently, allowing selection for specificity as well as affinity. To be useful in antibody isolation, it is important to recover the secreting cells following the analysis, not just to document their phenotypes. This property is achieved by supporting the cells on a membrane and capturing the secreted proteins after they pass through the membrane.

As a method to isolate antibodies of interest, this aspect of the invention provides substantial advantages. Antibody preparations ranging from crude antisera to highly purified recombinant polypeptides have been used in bioanalytical assays for the past half century. Natural antisera typically include extremely useful antibody species, but only a small amount of such antigen-specific antibody is present within a large excess of non-specific antibody. Techniques have been developed to isolate the specific antibodies through affinity purification on a sorbent coated with the antigen. Key to this process was identification of conditions for recovery of active antibody following elution, e.g., with a low pH buffer that gently disrupts the antibody-antigen complex.

Although affinity purification yields monospecific reagents (binding to one antigen), the underlying antibody population is polyclonal, and is therefore difficult to standardize for industrial scale assays or to manufacture on a scale suitable for use as a therapeutic. The development of monoclonal antibodies represented a major step forward in use of antibodies as assay reagents, delivering antibodies that recognize a single epitope on the antigen at a defined affinity. The standard approach to generate monoclonal antibodies, hybridoma technology, is time-consuming and labor-intensive, and can only be applied to a small subset of B-cells from an immunized host. The process involves isolating spleen cells from an immunized animal (generally a mouse) and fusing them to myeloma cells. For poorly understood reasons, antigen stimulated B-cells are preferentially represented in the resulting hybridomas. Still, the work load involved in growing, screening, and purifying hybridomas means that only a very small fraction of the underlying polyclonal response is effectively sampled in the hybridoma process, typically well under 1%. Rare clones, which may be the most useful, are thus lost.

One aspect of the invention is a screening methodology that enables superior identification of desired hybridomas. Immunization and cell fusion are conducted in the normal manner. Fused cells are distributed at high density into large culture wells with a membrane on the bottom. The membranes are designed to retain cells but to allow secreted proteins to pass through freely. Useful pore sizes range from 0.1 to 3 microns. The membrane chamber is positioned on a larger solid support of high protein-binding capacity such as polystyrene, or other suitable protein adsorbing material. The solid support may be pre-coated with an Ig capture reagent, e.g., antibody raised against immunoglobulin of the host species (goat anti-mouse, for example). After a sufficient level of secreted antibody has been captured, the top chamber containing the cells is gently removed from the support, preserving the living cells. The underlying support is then probed using a panel of binding reagents, each of which is labeled with a distinguishable particulate label.

The panel of binding reagents can include full-length antigen, antigen fragments containing specific epitopes, potentially cross-reactive molecules, and optionally anti-immunoglobulin (for quantifying the amount of captured antibody), as well as isotyping reagents (to distinguish the more useful IgG secreting cells from those secreting other isotypes). When a sample surface is found with a desirable binding profile (characterized by the set of labels that it has and has not bound), the physical coordinates of the spot are recorded, preferably by automated microscopy. The hybridoma residing at that coordinate is then recovered from the membrane bottomed culture plate. Both the number and type of particulate labels present are informative.

Figure 10:
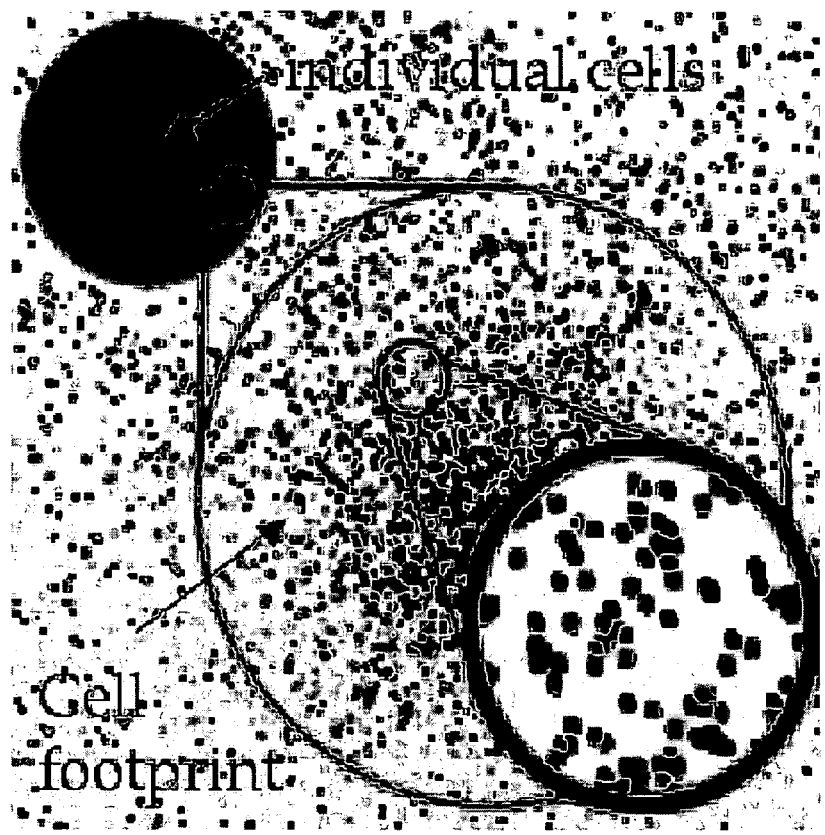
FIG. 10 shows the pattern of bound particulate labels obtained from an individual hybridoma cell resting on a membrane, with the secreted IgG captured on the underlying surface. This "footprint" has been probed with two distinguishable particulate labels. One particulate label (black) is conjugated to an anti-Ig reagent and is used to quantify the secretion level from the cell. A second particulate label (gray) is conjugated to an antigen and defines antigen specificity. With additional labels, multiple antigen specificities can be probed simultaneously.

Given the high sensitivity of the particulate label based detection system, it has proven possible to probe the secreted Ig from a single cell as illustrated in FIG. 10. The number of captured particulate labels is thus more directly related to intrinsic affinity of the interaction than is true for hybridoma screening for which the different growth rate and different secretion rate of particular clones are confounding variables when analyzing supernatants from individual wells. By adjusting the buffer conditions, a threshold of affinity can be imposed for a cell's secreted Ig to be scored as positive.

To illustrate this, two hybridoma lines were obtained from ATCC. One secretes antibody against myc peptide, the other against PSA. The myc peptide was conjugated to BSA which was then conjugated to particle type 1 (green); PSA was directly conjugated to particle type 2 (red). In addition, goat antibody against mouse IgG was conjugated to particle type 3 (pink). In all cases, the particle surface included aldehyde groups and the proteins were covalently attached by reductive amination. The anti-myc secreting cell line was spiked into the anti-PSA line as varying dilutions.

Illustrated in FIG. 10 are the cells on the membrane (gray circle, upper left corner), imaged using bright field microscopy. The underlying "footprint" for one cell is shown as the large circle with black and gray specks (corresponding to green and pink particles) whose density diminishes to background level outside that circle. In the inset at higher magnification, the individual black and gray objects correspond to the green and pink particles.

In detail, hybridoma cells were deposited onto a membrane with 0.4 μm pores that was in contact with an underlying polystyrene surface coated with Protein A. (Upper circle in FIG. 10.) Cells were suspended in 2% methylcellulose. To assure that all cells were firmly settled onto the membrane, the plate was briefly centrifuged. After centrifugation, the methylcellulose serves to hold the cells into a fixed position.

As secreted IgG diffused out of the hybridoma cells, a portion went through the membrane and was captured on the coated polystyrene surface. For these experiments, the membrane was supported using a plastic holder that allows the membrane to be gently removed from the polystyrene. The Transwell® from Costar® was adapted for this purpose by lowering the holder so that the membrane actually makes contact with the underlying polystyrene. To reduce noise from IgG that diffused laterally before going through the membrane, the methylcellulose matrix included Protein A conjugated to dextran.

After incubation for 4 hours, the membrane was removed and incubated in fresh growth media. The underlying polystyrene surface was incubated with the detection particles (green, red, pink). After washing, the surface was scanned at low magnification (macro lens, 1.5× zoom) using a Kramer M2 digital microscope. (Middle circle in FIG. 10.) Areas with high concentration of particles were readily identified by automated software. After switching to higher magnification (10× lens, 4× zoom), those spots were imaged in two color channels. (Lowest circle in FIG. 10.) Software identified each particle type as green, red, or pink and counted the number of particles of each type. A cell was deemed to be secreting anti-myc antibody if the green particles were approximately equal in number to the pink particles, with red particles at least 10 to 100-fold lower (background noise).

In this experiment, the anti-myc cells could be readily identified when spiked into the hybridoma mix at 1 in 10,000 cells. After identifying the location of the anti-myc secreting cells, several were recovered from the corresponding location on the membrane by a computer controlled micropipette. Alignment of the imaged polystyrene and the cells on the membrane was readily achieved by matching the geometric relations of the cells. After growth of the selected cells, the specificity for the myc antigen was confirmed by conventional Elisa methods.

Since the particulate label detection is so sensitive, the density of plated cells can be quite high. That is, non-secreting, or weak affinity, cells will be invisible in the primary assay, enabling the entire spleen population of B-cells to be screened. This feature represents a major advance over conventional hybridoma technology, eliminating the major limitation of hybridomas as compared to polyclonal sera. To screen these large numbers of cells, a pre-screen without the membrane can be used to identify wells with positive clones, which are then replated at lower density on membranes to facilitate single cell retrieval. Further, the background in the trans-membrane footprint can be reduced by including a sink for Ig (e.g., Protein A dextran) above the membrane; Ig that diffuses laterally before diffusing through the membrane is thereby minimized in favor of Ig that diffused directly through the membrane under the cell. Since B-cells are non-adherent cells, it is useful to embed the cells in a viscous medium, preferably one that is semisolid after cells have been deposited upon the membrane. When the membrane is moved, the cells thus retain their spatial location. Methylcellulose has proven to be an effective agent for this purpose. Thus, the cells are applied to the membrane as a dilute suspension of cells in methylcellulose, followed by centrifugation to deposit the cells on the membrane. The methylcellulose is semisolid and retains the cells in position. Recovery of cells by use of a micromanipulator is not impeded by this agent. Alternatively, laser capture microdissection techniques can be used to recover the desired cells. Both methods are suitable for automation.

In order to focus the resulting footprint and prevent overlap of footprints from adjacent cells, a capture reagent that is non-specific can be included in the methylcellulose matrix or deposited on top of it. If immunoglobulins are to be assayed on the sample surface, Protein A is an appropriate reagent for this purpose. The Protein A may also be coupled covalently to the matrix.

The types of particulate label present directly address the specificity of the antibody. As noted above, one of the attractive features of polyclonal sera is that highly specific antibody species are often present. Recovering those species in a standard hybridoma screen is difficult due to the low sampling rate, with specificity a secondary screening criterion. Further, the present method simplifies preparation of a family of antibodies with low intra-family cross-reactivity, since the specificity aspect is readily incorporated into the primary screen.

Still further efficiency improvements are attainable by immunizing a single mouse with 10 or more different antigens. The specific clones of interest are sufficiently rare that each can be identified among the population without creating an inordinate burden on the screening process or compromising the quality of clones ultimately generated against each antigen. Moreover, specificity can be evaluated early in the screening process. In one experiment, 7 peptides from a single protein were used as co-immunogens. Only 2 of the peptides elicited a strong enough response to yield detectable serum antibody in standard assays, yet cells secreting antibodies that recognized each of the 7 were found in the primary spleen population from the immunized mice. Since immunization with intact protein results in presentation of its fragments in vivo, this approach is able to capture rare specificities.

Because fusion to a myeloma cell is not necessary in order to get enough Ig to assay the specificity, alternative methods of immortalizing the recovered cells of interest are possible. One approach is to fuse individual B-cells to a myeloma using lasers, rather than bulk hybridoma formation using PEG or Sendai virus. Another approach is to clone the encoding DNA. Similarly, the entire process can be applied to proteins secreted from, e.g., microorganisms, or to Ig-like molecules captured from lysed cells (after first preparing a replicate plate of live cells). The recombinant antibodies in this aspect of the invention can be a product of the B-cell or hybridoma screen, or can be a library of random specificities as a primary source.

Non-Ig families of proteins prepared recombinantly can similarly be assessed for their ability to bind partners specifically. They can be analyzed as such or fused to a carrier. A preferred carrier is the Fc portion of Ig. This carrier is useful for attaining high secretion levels when the proteins are prepared recombinantly and for easy capture of the secreted protein on the underlying surface. As an example of a useful non-Ig protein family, we have used the avian pancreatic peptide described by Schepartz and colleagues (WO 01/81375). This 36-amino acid peptide spontaneously folds into a very stable tertiary structure, with a melting temperature of 65° C. Solvent exposed residues can be replaced with randomized amino acids without grossly affecting stability of the miniprotein. Fusion to Fc enables screening of recombinantly produced muteins by methods analogous to screening of hybridomas.

Employing cells on a membrane, with trans-membrane footprints analyzed after membrane is removed is thus useful to identify cells of interest which can then be recovered from the removed membrane. The use of this method is not dependent on the use of particulate labels, although particulate labels provide a preferred embodiment. When the desired components of the footprints comprise immunoglobulins, the footprint is improved by including protein A above the membrane.

Assay Modality 3. Cell Surface Antigen Constellation Analysis.

Cytokine secretion is a phenotype of multiple different types of T-cell (naïve, memory, killer) as well as other immune system cell types, such as dendritic cells. Surface antigenic markers have been found that demarcate these various cell types. Accordingly, it is useful to correlate the cytokine secretion profile with cell surface markers. Since the secretion profile can be conducted on cells plated on a membrane, the cells remain available for further analysis.

A specific application of cell surface staining is HLA typing. In this context, a particular cell will only bind two types of particulate label per locus (maternal and paternal alleles). Since some loci have hundreds of alleles, however, it is useful to have high multiplexing capacity.

A similar need for high multiplexing capacity in cell surface antigens is detection of shed tumor cells in blood (or urine, stool, lung lavage, etc.). Many tumors have distinctive combinations of normal cell surface antigens, as well as mutant forms of particular antigens. Thus, staining for a single cell surface marker is not sufficient to identify a cell as a tumor cell. However, if a blood sample contains 20 cells that have the same abnormal constellation of antigens, it is very likely that they are clonal descendents from a single tumor progenitor. With sufficient multiplexing capacity, normal cell types are all identifiable, making recognition of the abnormal cells more reliable.

Among the normal cell antigens of interest for characterizing tumors are those relevant to selecting therapy. For example, the MDR pump, if expressed at high levels in a tumor cell, is correlated with poor prognosis for drugs that are substrates for the pump. Similarly, if the estrogen receptor is expressed, the cells are more likely to respond to drugs such as tamoxifen. Thus, multiplexed cell staining can be used to define normal cell types, to define abnormal cell types, and to characterize functionally relevant antigens.

Thus, single cells or arrays of individual cells on membranes may be immersed in a complex mixture of specific binding partners for these markers, each specific binding partner coupled to a particulate label with a different hue. In this manner, a complex complement of receptors available on a single cell can be ascertained, and multiple cell samples from particular tissues can be sorted for heterogeneity.

Assay Modality 4: Characterization of Clinical Samples

Disease conditions and their response to treatment by therapeutic protocols are characterized by a multiplicity of parameters, including translocation of proteins intracellularly, changes in surface antigen profiles and changes in secretion profiles. Cells characteristic of disease states may display such typical patterns—for example, tumor cells for any particular type of tumor will have a characteristic pattern of surface antigens; the progress of treatment can be monitored by the fate of cells with this pattern. The following examples are illustrative of the type of characterization made possible by the methods of the invention as applied to clinical samples.

Disease conditions can be characterized by changes in the T-cell population in an affected subject. Such a subject may be any mammal; the method is of particular interest when applied to humans but is equally applicable in veterinary contexts for domestic and farm animals, in particular. In one embodiment of characterizing a disease state, the T-cell profile of the subject is obtained. The profile can be monitored as a function of treatment protocols, and the data thus generated are useful both in informing the practitioner of the progress and effectiveness of treatment and, on a more industrial scale, in evaluating candidate drugs and protocols for future clinical use.

Because the cells can be recovered and then treated using various protocols, the effects of a single drug or a combination of drugs on the cells can be investigated. Alternatively, aliquots of the human specimen can be treated in parallel experiments to explore different conditions. For example, to investigate the effect of a drug on the cytokine secretion profile, a population of T-cells is plated, after which the cells are exposed to the drug, and the secreted proteins captured on the plate. The frequency and character of the changes induced are then recorded. Other perturbants can also be analyzed in this manner, e.g., hormones, other cells, toxins. For example, the perturbant could be a cosmetic whose skin irritancy properties are under investigation, with the T-cell population drawn from test subjects as an alternative to animal testing.

For clinical studies, typically, profiles of cytokine secretion are obtained for a representative sample of the T-cell population. Generally, sample sizes of 50, preferably 100, and more preferably 1,000 individual T-cells should be profiled in order to ascertain a characteristic picture of the T-cell population. By the term "characterizing the T-cell population of a subject" refers to obtaining profiles of cytokine secretion of a representative sample of said T-cell population.

As noted above, the impact of various treatment protocols, including individual drugs and drug combinations can be tested for the effects on the T-call population profile in a subject. In addition, other indicators of clinical effectiveness can be used. For example, intracellular translocation of proteins, the distribution and type of surface displayed proteins, and secretion profiles in general may characterize particular disease states and the effect of drugs on these disease states may be tested as described in U.S. Pat. No. 6,673,554.

Assay Modality 5. Tissue Paints.

The utility of multiplexed staining is not limited to defining cell types in blood specimens, but is more broadly applicable to any histological context. For demarcating cell types in order to simplify automated pathology, for example, any antigen is useable, not just cell surface antigens. Tissue slices, for instance, can be stained with particulate label conjugated antibody and observed microscopically. Various intracellular antigens can be demarcated, including nuclear envelope antigens, Golgi apparatus, and microtubules. Just as tumor cells can display normal antigens in abnormal constellations, so too can intermediate stage stem cells (indeed, some tumors are thought to be the result of disregulation of this type of stem cell). By identifying normal cells with a multivariate staining protocol, such unusual cells are more readily discovered.

Tissue paints are also useful in elucidating the interaction of cell types in tissue level processes such as angiogenesis or regeneration. These processes involve multiple cell types, each secreting factors that influence the surrounding cells.

For purposes of tissue painting, mRNA can be used as markers instead of protein antigens, with a complementary probe on a particulate label. Single mRNA molecules have been imaged in cells, by self-assembling a complex of fluors at the site to yield a highly localized concentration of fluors analogous to the fluor concentration within a particulate label. The technique was used to demonstrate that mRNA from different genes have different spatial localizations within the cell (U.S. Pat. No. 5,641,675). Extension to multiplexed labels and to tissue painting are not disclosed in this patent.

Particulate labels can also be used as retrograde transport labels. In this technique, particulate labels are taken up into a nerve cell by endocytosis, and transported back up the axon to the cell body. In conventional retrograde labeling to map out neuronal circuits, the efficiency of endocytotic uptake is deliberately kept low so as to label only a few cells per experiment. With particulate labels available in a rainbow of hues, a field of nerve endings can be exposed to a rainbow spread of particulate labels, and the full circuitry analyzed in a single animal, which is more accurate than collating data from separate animals. Similarly, particulate labels can be injected into a cell body. If the particulate label is coated with a protein that promotes transport along the microtubules, then the circuitry can be mapped in an anterograde fashion as well. The observation of single cells using microscopy permits the observer to note the locations of multiple cellular components.

Similarly, each cell of an early stage embryo can be loaded with a different particulate label type, and the process of morphogenesis tracked. The number of progeny cells that can be identified is limited by the partitioning of the particulate labels, but as only a few particulate labels are needed in a given cell to identify the hue accurately, several generations can be observed. Alternatively, enhancer trap constructs have previously been used to label cells for elucidating embryogenesis. In this technique, a reporter gene such as luciferase or beta-galactosidase, is cloned at random into a germ line chromosomal site. If the reporter comes under control of a transcription promoter that is specific to a particular lineage, then the cells of that lineage will be labeled. With the added multiplexing provided by particulate labels, hundreds of distinguishable antigens can be used as reporters. Similarly, the reporters can be engineered using a secreted protein as the carrier for a series of epitope tags (distinguishable short peptides). Applied to tissue culture cells, this approach to multiplexed gene reporter assays enables many pathways to be interrogated concurrently, for study of pathway interactions. As noted above with regard to screening miniproteins such as avian pancreatic peptide, Fc portion of antibody provides a suitable carrier for the epitope tags.

As still another example, the early embryo of *Drosophila* uses ~30 genes to create the basic segmentation plan. The gene products have been studied by immunohistochemical staining, three at a time, in order to visualize the process. Considerable effort is required to align the maps created in this fashion. With the same 30 antibodies each attached to a different particulate label, the entire map can be constructed in one embryo, providing greater insight into the effects of mutations.

Assay Modality 6. Growth Factor Discovery.

It is believed that more than 5,000 genes encode secreted proteins. Only a small fraction have been well characterized. Their roles in autocrine and paracrine cell signaling can be studied by the methods discussed above under "Tissue Paints," but only after some preliminary identification of what factors are relevant to what tissues. One property to examine is trophic or growth stimulatory effects. An efficient approach to studying the effect of a putative trophic factor on many different cell types is to expose embryoid bodies to the factor. As described in U.S. Pat. No. 5,914,268, dissociation of a mammalian embryo at the 8-cell stage into media with the appropriate protein factors leads to mitotic proliferation as undifferentiated stem cells. Upon withdrawal of a necessary factor, the cells form clumps, typically solid or hollow spheres of ~500 cells, and proceed to differentiate. Numerous cell types are formed, but in a disorganized fashion. A single 96-well microplate well can hold hundreds of these embryoid bodies. For purposes of discovering growth factors, the mouse (or man) has effectively been shrunk down to a single microplate well. In order to exploit this miniaturization, a highly sensitive means is needed for quantifying the dozens to hundreds of cell types. With particulate labels as labels, it is possible to examine all the cell types for which specific antibodies are available. Antigens can be cell surface or intracellular. Cell surface antigens also facilitate recovery of the cells for further analysis.

Using the antibody isolation technology described above, hundreds or even thousands of antigens can be screened concurrently, with secondary screening on embryoid bodies providing a means of finding suitable tissue paints for this purpose and for automated pathology in general. Further, as a tertiary screen, antibodies attached to particulate labels can be probed in a multiplexed fashion against tissue arrays (samples of all tissues from a mouse or man). Such a screen will reveal intermediate stage stem cells. Growth factors active in the embryoid body context can then be tested for their impact on the growth of the putative intermediate stage stem cells. Such growth factors have potential utility for inducing regeneration or wound healing. Conversely, neutralizing antibodies (or receptor domains) can be used to reduce activity, as a treatment for proliferative disorders, including cancer.

Thus, an embryoid body is labeled with a multiplicity of distinguishable particulate labels each having a specific binding partner for a marker for an individual type of cell contained in the embryoid body. This "control" type embryoid body is compared to a test embryoid body which has been treated with a candidate compound and then labeled in a manner similar to that of the "control." Comparison is then made with regard to the number and type of each cell that has been labeled in the "control" as compared to the test embryoid body. A candidate compound which results in the expansion or proliferation of at least one cell type in the test antibody as compared to the "control" is then identified as a growth factor for that cell type. In this way, a multiplicity of different cell types can be tested simultaneously for a response to a single candidate compound.

Assay Modality 7. Multiplexed Detection of Fractionated Biomaterials.

Fractionation methods entail a diverse group of techniques used to separate mixtures of substances based on differences in their intrinsic molecular properties, including size, charge, and relative affinities of the substances for a mobile phase (a moving gas or fluid) and a stationary phase (sorbent, including a porous solid or gel or a liquid coated on a solid support). In the latter cases, the rate at which each substance in carried along by the mobile phase depends on its solubility (in a liquid mobile phase) or vapor pressure (in a gas mobile phase) and on its affinity for the sorbent. Related techniques based on other physical properties such as charge or size include, but are not limited to 1D gels, 2D gels, agarose gels, and capillary electrophoresis.

Perhaps the simplest fractionation method is separation of soluble and insoluble proteins following cell disruption. Applied to cells obtained by laser capture microdissection (U.S. 2204/0053326 A1), this method allows multiple signaling pathway proteins to be analyzed on minute quantities of material. If the cells are disrupted in situ on a capture surface, directly or after diffusion through a membrane, a multiplexed ELISA-style assay can be conducted at the single cell level.

Electrophoresis is used to separate complex mixtures of proteins (e.g., from cells, subcellular fractions, column fractions, or immunoprecipitates), to investigate subunit compositions, and to verify homogeneity of protein samples. In polyacrylamide gel electrophoresis, analytes migrate in response to an electrical field through pores in the gel matrix; pore size decreases with higher acrylamide concentrations. The combination of gel pore size and protein charge, size, and shape determines the migration rate of the protein. Variations known in the art include ultrathin gels, multiple single-concentration gels, gradient gels, and multiple gradient gels and minigels; gels can also be run in 2 dimensions, with a first separation based on isoelectric point, for example, followed by a second dimension based on size, for example. Analytes separated on gels can be subsequently analyzed in situ by autoradiography or phosphor imaging, or staining with dyes.

Greater flexibility in analysis is provided by blotting (transfer from the gel to a membrane, either by diffusion, wicking, or migration under the influence of an electric field). In the case of DNA, it is referred to as southern blotting; in the case of mRNA, as northern blotting, and in the case of proteins, as western blotting. Suitable membranes include nitrocellulose, PVDF, or nylon. The transferred analytes are bound to the surface of the membrane, providing access for reaction with detection reagents. All remaining binding sites are blocked by immersing the membrane in a solution containing either a protein or detergent blocking agent. Once immobilized on a membrane, analytes can be probed with biospecific binding agents conjugated to particulate labels.

Multiplexed staining is useful for correlating different properties on a single sample. Instead of running replicate samples in adjacent lanes, each stained for a different property, the adjacent lanes can be used to compare samples whose source cells had been isolated before and after treatment with a drug or other perturbant, or to compare normal and diseased tissue and the like. Properties of interest to examine on the same specimen, typically with antibodies to the feature, include, but are not limited to: phosphotyrosine and phosphoserine; sequence "motifs" including zinc finger or leucine zipper motifs; SH2 domains and other protein interaction domains; engineered tags such as c-myc, His-tag, FLAG epitope; and specific carbohydrate moieties (using lectins in place of antibodies, for example). The art of analyte detection on blots is extensive. In all cases, the use of multiplexed particulate labels allows more information to be gained from the same sample, and reduction in apparatus size. In particular, advances in microfabrication are leading to drastic reduction in size of gel electrophoresis, from tens of centimeters to millimeters.

Although multiplexed staining has been described, the identification of analytes in gel fractionated and blotted specimens by cataloging individual particulate labels has not. One application employs one of the numerous protein size ladders available from commercial sources. There are critical to accurate determination of analyte molecular weight. A kit from Invitrogen, for example, consists of 10 proteins for a sizing ladder ranging in apparent molecular weight from ~10 to 190 kDa. In standard practice, the sizing ladder is run as a separate lane, and stained non-specifically for protein. With particulate labels, the 10 proteins can all be modified to bind a particular particulate label, pre or post separation as appropriate. Thus, the sizing ladder can be included in each and every lane, providing far more precise alignment with the analytes. The same benefit accrues to DNA sizing ladders.

Capillary electrophoresis (CE) is another fractionation technique in widespread use, especially for DNA sequencing (Carrilho, F., *Electrophoresis* (2000) 21:55-65) and fragment-size analysis (Butler, J. M., *Methods Mol. Biol.* (1998) 98:279-289). For example, sequencing by the chain-termination method involves the synthesis of a DNA strand by a DNA polymerase using a single stranded template and a specific primer. The synthesis reaction ends upon incorporation of a nucleotide analog (ddNTP) that terminates elongation. When proper mixtures of dNTP's and one of the four ddNTP's are used, polymerization will be terminated randomly at each possible site. In current commercial sequencers (e.g., the ABI 373 from Applied Biosystems), the chain terminators are also labeled with one of four distinguishable organic dye fluors. Use of quantum dots as the fluors increases sensitivity.

With eight distinguishable quantum dots, two DNA strands can be sequenced in a single capillary. Much higher degrees of multiplexing are available in a post-separation labeling mode. The separated DNA is deposited on a membrane, either by dripping out of the end of the capillary onto a moving drum, or by the older technique of gel electrophoresis separation followed by southern blotting, the efficiency of which is improved by using very thin gels; thin gels have lower capacity, but since detection is so sensitive, that is acceptable. If DNA sample #1 is initiated with a primer that includes a unique sequence (18 bases is sufficient in the human genome), then the complementary sequence can be attached to particulate label #1. With hundreds of distinguishable particulate labels, hundreds of DNA fragments can be distinguished in a single lane, representing a radical increase in throughput. Since the particulate labels are bright enough that detection of analyte approaches the single molecule level, this technique is particularly useful for DNA that is only available in trace amounts, or to avoid cumbersome amplification of the DNA by PCR or cloning prior to sequencing. As a post-separation labeling approach, use of particulate labels as tags also avoids artifacts associated with the fluorescent dye terminators altering migration rates of the DNA's.

Performance of capillary electrophoresis in micro-fabricated devices has been shown to decrease the electrophoresis time without any significant loss in resolution (see Medintz, I. L., et al., *Electrophoresis* (2001) 22:3845-3856 and Jin, L. J., et al., *Biotechniques* (2001) 31:1332-1340, 1342 for recent reviews). DNA sequencing with read lengths of approximately 500 bp can be performed in less than 30 min (reviewed in Medintz, I. L., et al, *Electrophoresis* (2001) 22:3845-3856). The high sensitivity provided by particulate labels is of particular value in this context, as miniaturization reduces the loading capacity for the DNA.

In addition, peptides and other oligomers with a wide variety of specificities can be constructed using combinatorial techniques to obtain panels of paralogs with widely differing binding specificities (U.S. Pat. No. 5,340,474). In general, multiplexed ELISA style assays, shrunk down to microscopic scale, are useful for measuring blood, urine, etc., biomarkers. The Growth Factor Discovery modality should yield numerous proteins whose elevated level in blood is an early warning signal for cancer.

SUMMARY OF THE SUBJECT MATTER

In one aspect, the invention relates to a method to obtain a sample that may be used in characterizing a subset of components associated with an individual cell, which method comprises supporting said cell on a permeable membrane support, said support having been overlaid on a sample surface, and allowing cellular components to penetrate the membrane and be deposited on the sample surface, whereby the location of said cell on the membrane and the location of the sample surface may be correlated, thereby obtaining a sample of components associated with said individual cell.

This method is further characterized as that wherein said membrane support is coated with a matrix that is sufficiently semisolid to maintain the position of the cell deposited on the membrane, especially wherein the matrix is comprised of methylcellulose.

This method may further include examining the sample surface microscopically to determine the components present on said sample surface, in particular when more than two components are determined, or when said components on said surface are labeled with particulate labels, said each label comprising a specific binding partner for a component and having a characteristic hue, and optionally wherein the presence and amount of each component is determined to obtain a profile of said cell with respect to said components.

When the method includes examining the sample surface, the components may be products of reporter genes, or when the cell is a T-cell, the components comprise at least three different cytokines, especially as performed on at least 50 T-cells representative of the T-cell population of a subject for whom a disease state is to be assessed.

In some embodiments the cell is lysed, especially a lysed bacterium.

Alternatively, the cell is a primary B-cell, an immortalized B-cell or a hybridoma and the components to be determined are antibodies specific for a specific antigen or epitope.

In this instance, the matrix may be associated with a substance that binds antibodies nonspecifically, e.g., Protein A.

The method may be applied to drug or reaction-to-stimulus testing if it further includes exposing said cell to a drug or other external stimulus prior to labeling the cell with particulate labels, preferably when said cell is contained in a tissue sample and/or multiple doses of drug are employed.

In this assay, the number and nature of particulate labels observed under conditions where said cell has not been exposed to said drug or stimulus is compared to the number and nature of particulate labels observed when the cell has been exposed to said drug or external stimulus, thereby determining the effect of said drug or external stimulus on said cell.

In another aspect, the invention is directed to a method to determine the presence or absence of a multiplicity of cellular components associated with a single cell, which method comprises contacting said single cell or components thereof with a multiplicity of particulate labels with different hues, wherein each differently hued particle is conjugated to specific binding partner for a cellular component; and wherein said single cell is disposed, or said components are disposed, on a sample surface which retains said components but which does not retain unbound particulate labels;

removing unbound particulate labels; and observing the number and nature of particulate labels associated with said cell or components on the sample surface by means of microscopic observation. Optionally, the presence and amount of each component is determined to obtain a profile of said cell with respect to said components.

In this embodiment, the components may be products of reporter genes, or the cell may be a T-cell and the components comprise at least three different cytokines, optionally performed on at least 50 T-cells representative of the T-cell population of a subject for whom a disease state is to be assessed.

As in the previous embodiment, the cell may be lysed and may be a lysed bacterium.

Alternatively, the cell is a primary B-cell, an immortalized B-cell or a hybridoma and the components to be determined are antibodies specific for a specific antigen or epitope.

Also, this may further include exposing said cell to a drug or other external stimulus prior to said contacting with particulate label optionally wherein said cell is contained in a tissue sample and/or multiple doses of drug are employed.

The number and nature of particulate labels observed under conditions where said cell has not been exposed to said drug or stimulus may then be compared to the number and nature of particulate labels observed when the cell has been exposed to said drug or external stimulus, thereby determining the effect of said drug or external stimulus on said cell.

The invention also concerns a method to obtain a profile of components of a single cell, which method comprises providing a sample of such components with a multiplicity of particulate labels, each label having a specific binding partner for a component to be determined and having a characteristic hue, and observing the association of said labels with the components of said single cell microscopically, and assessing the number of particles associated with each component of said cell, thereby obtaining a profile of the components of a single cell, optionally, wherein said profile is represented by a location in n-dimensional space, wherein n is the number of components for which specific binding partner-containing particulate labels have been supplied.

Here, too, the cell may be a T-cell and the components comprise at least three different cytokines, optionally performed on at least 50 T-cells representative of the T-cell population of a subject for whom a disease state is to be assessed.

In the alternative, the cell is a B-cell and the components to be determined are antibodies specific for a specific antigen or epitope. In a preferred embodiment, at least one particulate label binds antibody specific for an antigen and at least one label binds antibodies regardless of antigen specificity.

As in the previous embodiments, the method further includes exposing said cell to a drug or other external stimulus prior to said providing of label, preferably where the cell is contained in a tissue sample and/or multiple doses of drug are employed.

The number and nature of particulate labels observed under conditions where said cell has not been exposed to said drug or stimulus may then be compared to the number and nature of particulate labels observed when the cell has been exposed to said drug or external stimulus, thereby determining the effect of said drug or external stimulus on said cell.

The invention also concerns a method to identify cells that can be immortalized to secrete a desired immunoglobulin, which method comprises testing individual B-cells derived from spleen, lymph nodes, mucosal-associated lymphatic tissue or peripheral blood for secretion of antibody for an antigen or epitope by treating each said B-cell with at least a first particulate label comprising a first specific binding partner for immunoglobulins that is not antigen or epitope dependent and with at least a second particulate label comprising a second specific binding partner for immunoglobulin specific for said antigen or epitope; and determining microscopically the number of said first and second particulate labels associated with said cell, whereby cells associated with approximately equal numbers of said first and second labels are identified as cells that can be immortalized to secrete said immunoglobulin.

This method can be performed so that each said cell is supported on a membrane and any secreted antibodies are collected at a sample surface below said membrane.

In this case, it may be performed on an array of individual B-cells so the location of the sample surface can be correlated with the position of each cell on the membrane.

The membrane may further contain a matrix to secure the cell to the membrane, as well as a reagent that binds to immunoglobulins in an antigen and epitope independent manner.

The method may further include immortalizing the B-cells identified as secreting desired immunoglobulins.

Also included in the invention is a method to identify cells that secrete an immunoglobulin of desired specificity and affinity which method comprises providing cells on a membrane, said membrane being permeable to secreted immunoglobulins and said membrane overlaying a sample surface optionally comprising a capture reagent for immunoglobulins;

removing the membrane containing the cells; and probing the sample surface with a multiplicity of epitopes and antigens each labeled with a distinguishable particulate label; and selecting a location of the surface which binds to desired epitopes and antigens, but not undesired epitopes and antigens; and correlating the location of the surface thus identified with the location of cells on the membrane.

The cells may be arranged on said membrane as an array of single cells, and the B-cells may be derived from spleen or plasma of an immunized vertebrate.

In another aspect, the invention concerns a particulate label which comprises a first particle having a characteristic hue further coupled at its surface to a multiplicity of second particles of diameters smaller than that of said first particle, wherein said second particles have different hues from said first particle and from each other.

Preferably, said first particle has a diameter of 200-500 nm and said second particles have diameters of 10-100 nm. The said second particles may be coupled to the surface of said first particles through a covalent linkage, and/or each of said hues is generated by at least two signal generating moieties. The signal generating moieties may bee fluorophores.

A collection of these particulate labels which comprises a multiplicity of said first particles of different hues is also included in the invention.

The invention also includes a method to detect the presence or absence of a multiplicity of components in a solubilized biological sample which comprises separating components of the solubilized biological sample in a single migration path by electrophoresis or chromatography, wherein said components are labeled with particulate labels such that each component has an associated characteristic hue by virtue of its particulate label; and detecting the characteristic hues of the separated components at their respective positions in said migration path by means of microscopic observation, thereby detecting the presence or absence of each component.

One important application is that wherein said components are associated with ddNTP's and said separating is conducted as part of a sequencing determination.

In another aspect, the invention relates to a method to characterize a tissue sample which method comprises contacting said sample with a multiplicity of particulate labels, each label comprising a specific binding partner for a component of said tissue and having a characteristic hue; and observing said tissue sample microscopically, to determine the number and location of each particulate label.

The invention also includes a method to identify growth factors important in embryonic development which method comprises labeling at least a first and second embryoid body with a multiplicity of particulate labels, each label comprising a specific binding partner for a cell type of said embryoid body and having a characteristic hue; wherein said first embryoid body has been treated with a candidate growth factor, and comparing the number of at least two types of cells in said first and second embryoid body;

whereby an increase in the number of a cell type in said first as compared to said second embryoid body identifies said candidate compound as a growth factor for said cell type.

Finally, the invention includes a method to remove a membrane from a sample surface while minimizing turbulence at the surface of the membrane, which method comprises lifting said membrane from a sample surface that has been provided an aperture to minimize suction, as well as an apparatus for conducting studies on a sample surface which assay comprises removal of a membrane containing cells from said surface, which apparatus comprises a sample well provided with an aperture adjacent said sample surface.

The invention claimed is:

1. A method to determine the presence, absence or amount of each of a multiplicity of components released from a single cell and/or the nature of at least one released component from the single cell, which method comprises permeabilizing or lysing the single cell or allowing the single cell to secrete cellular components, disposing the released components, on a planar sample surface, contacting the released components disposed on said surface with a multiplicity of particulate labels having diameters of 10-500 nm with different hues, wherein each differently hued particle is conjugated to specific binding partner for a cellular component or portion thereof; and wherein particulate labels bound to components are retained but particulate labels not bound to components are not retained;

removing particulate labels not bound to components; and observing the number and nature of individual particulate labels that are bound to the released components on the sample surface by means of microscopic observation, whereby the presence, absence or amount of each of a multiplicity of released components and/or the nature of at least one released component from said single cell are determined.

2. The method of claim 1, wherein the amount of each different released component is assembled to obtain a profile of said cell with respect to said released components, wherein said profile is represented by a location in n dimensional space, wherein n is the number of components for which specific binding partner-containing particulate labels have been supplied.

3. The method of claim 2, wherein the cell is a T-cell and the released components comprise at least three different cytokines.

4. The method of claim 3, which is performed on at least 50 T-cells representative of the T-cell population of a subject for whom a disease state is to be assessed.

5. The method of claim 2, which further includes exposing said cell to a drug or other external stimulus prior to said contacting.

6. The method of claim 5, wherein said cell is obtained from a tissue sample.

7. The method of claim 5, wherein the number and nature of particulate labels observed under conditions where said cell has not been exposed to said drug or stimulus is compared to the number and nature of particulate labels observed when the cell has been exposed to said drug or external stimulus, thereby determining the effect of said drug or external stimulus on said cell.

8. The method of claim 1, wherein the released components are products of reporter genes.

9. The method of claim 1, wherein the cell is a T-cell and the released components comprise at least three different cytokines.

10. The method of claim 9, which is performed on at least 50 T-cells representative of the T-cell population of a subject for whom a disease state is to be assessed.

11. The method of claim 1, wherein the cell is a primary B-cell, an immortalized B-cell or a hybridoma and the component the nature of which is to be determined is an antibody specific for a specific antigen or epitope.

12. The method of claim 1, which further includes exposing said cell to a drug or other external stimulus prior to said contacting.

13. The method of claim 12, wherein said cell is obtained from a tissue sample.

14. The method of claim 12, wherein the number and nature of particulate labels observed under conditions where said cell has not been exposed to said drug or stimulus is compared to the number and nature of particulate labels observed when the cell has been exposed to said drug or external stimulus, thereby determining the effect of said drug or external stimulus on said cell.

15. The method of claim 1, wherein said cell is lysed or permeabilized.

16. The method of claim 1, wherein said released components are secreted components.

17. The method of claim 1, wherein said single cell is supported on a permeable membrane support which is overlaid on said sample surface on which said released components are deposited.

18. The method of claim 17 which is performed on an array of individual cells and wherein the location of the sample surface is correlated with the position of each cell on the membrane.

* * * * *